(12) United States Patent
Guerrant et al.

(10) Patent No.: US 9,387,199 B2
(45) Date of Patent: Jul. 12, 2016

(54) COMPOSITIONS AND METHODS FOR TREATING CLOSTRIDIUM INFECTION AND PREVENTING RECURRENCE OF INFECTION

(71) Applicant: University of Virginia Patent Foundation, Charlottesville, VA (US)

(72) Inventors: Richard L. Guerrant, Charlottesville, VA (US); Cirle Alcantara Warren, Waynesboro, VA (US); John Hudson Moore, II, Richmond, VA (US); Edward van Opstal, Great Falls, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/539,214

(22) Filed: Nov. 12, 2014

(65) Prior Publication Data
US 2015/0133366 A1    May 14, 2015

Related U.S. Application Data

(60) Provisional application No. 61/902,842, filed on Nov. 12, 2013.

(51) Int. Cl.
| | |
|---|---|
| *A61K 38/14* | (2006.01) |
| *A61K 31/4188* | (2006.01) |
| *A61K 31/7028* | (2006.01) |
| *A61K 31/4174* | (2006.01) |
| *A61K 31/426* | (2006.01) |

(52) U.S. Cl.
CPC ......... *A61K 31/4188* (2013.01); *A61K 31/4174* (2013.01); *A61K 31/426* (2013.01); *A61K 31/7028* (2013.01); *A61K 38/14* (2013.01)

(58) Field of Classification Search
None
See application file for complete search history.

(56) References Cited

U.S. PATENT DOCUMENTS

| | | | |
|---|---|---|---|
| 4,938,949 A | 7/1990 | Borch et al. | |
| 5,736,139 A * | 4/1998 | Kink | C07K 14/245 424/164.1 |
| 2009/0324736 A1* | 12/2009 | Johnson | A61K 31/00 424/606 |

OTHER PUBLICATIONS

Chen et al. ,"A Mouse Model of Clostridium difficle-Associated Disease", Gastroenterology, 2008, pp. 1984-1992.*
Warren et al., "Amixicile, a Novel Inhibitor of Pyruvate:Ferredoxin Oxidoreductase, Shows Efficacy against Clostridium difficile in a Mouse Infection Model", Antimicrobial Agents and Chemotherapy, Aug. 2012, p. 4103-4111; Published ahead of print May 14, 2012.*
Swanson et al, "In Vitro and In Vivo Evaluation of Tiacumicins B and C against Clostridium difficile", Antimicrobial Agents and Chemotherapy, 1991, pp. 1108-1111.*
Anton et al.,"Rifalazil Treats and Prevents Relaspe of Clostridium difficile-Associated Diarrhea in Hamsters", Antimicrobial Agents and Chemotherapy, 2004, pp. 3975-3979.*
Should. Dictionary.com. Dictionary.com Unabridged. Random House, Inc.http://dictionary.reference.com/browse/should (accessed: Sep. 4, 2015); p. 1/7.*
Musher et al., "Nitazoxanide versus Vancomycin in Clostridium difficile Infection: A Randomized, Double-Blind Study", Clinical Infectious Diseases 2009; p. e41-6.*
Sun et al., Recent Development in the Treatment of Clostridium difficile Associated Disease (CDAD), 2008, Annual Reports in Medicinal Chemistry, vol. 43, 269-277.*
Cohen SH, Gerding DN, Johnson S, Kelly CP, Loo VG, McDonald LC, Pepin J, Wilcox MH. 2010. "Clinical practice guidelines for Clostridium difficile infection in adults: 2010 update by the Society for Healthcare Epidemiology of America (SHEA) and the Infectious Diseases Society of America (IDSA)", Infect Control Hosp. Epidemiol. 31:431-455. doi:10.1086/651706.
Surawicz CM, Alexander J. 2011. :Treatment of refractory and recurrent Clostridium difficile infection, Nat. Rev. Gastroenterol. Hepatol. 8:330-339. doi:10.1038/nrgastro.2011.59.
Pepin J, Alary ME, Valiquette L, Raiche E, Ruel J, Fulop K, Godin D, Bourassa C. 2005, "Increasing risk of relapse after treatment of Clostridium difficile colitis in Quebec, Canada", Clin. Infect. Dis. 40:1591-1597. doi:10.1086/430315.
Lagrotteria D, Holmes S, Smieja M, Smaill F, Lee C. 2006, "Prospective, randomized inpatient study of oral metronidazole versus oral metronidazole and rifampin for treatment of primary episode of Clostridium difficile-associated diarrhea", Clin. Infect. Dis. 43:547-552. doi:10.1086/506354.
Musher DM, Aslam S, Logan N, Nallacheru S, Bhaila I, Borchert F, Hamill RJ. 2005, "Relatively poor outcome after treatment of Clostridium difficile colitis with metronidazole". Clin. Infect. Dis. 40:1586-1590. doi:10.1086/430311.
Zar FA, Bakkanagari SR, Moorthi KM, Davis MB. 2007, "A comparison of vancomycin and metronidazole for the treatment of Clostridium difficile-associated diarrhea, stratified by disease severity", Clin. Infect. Dis. 45:302-307.
Louie TJ, Miller MA, Mullane KM, Weiss K, Lentnek A, Golan Y, Gorbach S, Sears P, Shue YK. 2011, "Fidaxomicin versus vancomycin for Clostridium difficile infection", N. Engl. J. Med. 364:422-431. doi:10.1056/NEJMoa0910812.
Garey KW, Jiang ZD, Bellard A, Dupont HL. 2008, "Rifaximin in treatment of recurrent Clostridium difficile-associated diarrhea: an uncontrolled pilot study", J. Clin. Gastroenterol. doi:10.1097/MCG.0b013e31814a4e97.

(Continued)

*Primary Examiner* — Lianko Garyu
(74) *Attorney, Agent, or Firm* — Rodney L. Sparks

(57) ABSTRACT

*C. difficile* infection (CDI) is the most common cause of antibiotic-associated diarrhea. Unfortunately, antibiotic therapy remains as the standard treatment for this antibiotic-induced disease and relapses are common. Antibiotic treatment typically is given for 10 to 14 days for initial or second episode of CDI. For recurrent episodes, more prolonged courses are recommended. It is disclosed herein that lower dose or shorter course of the antimicrobial treatment is sufficient to treat the disease and prevent recurrent disease by enabling a good immunologic response to infection, and perhaps also by better preserving normal flora, thus protecting against relapses or reinfection.

7 Claims, 11 Drawing Sheets

(56) References Cited

OTHER PUBLICATIONS

Musher DM, Logan N, Mehendiratta V, Melgarejo NA, Garud S, Hamill RJ. 2007. Clostridium difficile colitis that fails conventional metronidazole therapy: response to nitazoxanide. J. Antimicrob. Chemother. 59:705-710. doi:10.1093/jac/dkl553.

Warren CA, OEvan Ballard TE, Kennedy A, Wang X, Riggins M, Olekhnovich I, Warthan M, Kolling GL, Guerrant RL, Macdonald TL, Hoffman PS. 2012. "Amixicile, a novel inhibitor of pyruvate:ferredoxin oxidoreductase, shows efficacy against Clostridium difficile in a mouse infection model", Antimicrob. Agents Chemother. 56:4103-4111. doi:10.1128/AAC.00360-12.

Johnson S, Schriever C, Galang M, Kelly CP, Gerding DN. 2007, "Interruption of recurrent Clostridium difficile-associated diarrhea episodes by serial therapy with vancomycin and rifaximin", Clin. Infect. Dis. 44:846-848. doi:10.1086/511870.

Musher DM, Logan N, Bressler AM, Johnson DP, Rossignol JF. 2009, "Nitazoxanide versus vancomycin in Clostridium difficile infection: a randomized, double-blind study", Clin. Infect. Dis. 48:e41-e46. doi:10.1086/596552.

Sun X, Wang H, Zhang Y, Chen K, Davis B, Feng H. 2011, "Mouse relapse model of Clostridium difficile infection", Infect. Immun. 79:2856-2864. doi:10.1128/IAI.01336-10.

Hecht DW, Galang MA, Sambol SP, Osmolski JR, Johnson S, Gerding DN. 2007, "In vitro activities of 15 antimicrobial agents against 110 toxigenic Clostridium difficile clinical isolates collected from 1983 to 2004", Antimicrob. Agents Chemother. 51:2716-2719. doi:10.1128/AAC. 01623-06.

Baines SD, O'Connor R, Saxton K, Freeman J, Wilcox MH. 2009, "Activity of vancomycin against epidemic Clostridium difficile strains in a human gut model", J. Antimicrob. Chemother. 63:520-525. doi:10.1093/jac/dkn502.

Babakhani F, Bouillaut L, Gomez A, Sears P, Nguyen L, Sonenshein AL. 2012, "Fidaxomicin inhibits spore production in Clostridium difficile", Clin. Infect. Dis. 55(Suppl 2):S162-S169. doi:10.1093/cid/cis453.

Edlund C, Barkholt L, Olsson-Liljequist B, Nord CE. 1997, "Effect of vancomycin on intestinal flora of patients who previously received antimicrobial therapy", Clin. Infect. Dis. 25:729-732.

Louie TJ, Emery J, Krulicki W, Byrne B, Mah M. 2009, "OPT-80 eliminates Clostridium difficile and is sparing of Bacteroides species during treatment of C. difficile infection", Antimicrob. Agents Chemother. 53:261-263. doi:10.1128/AAC.01443-07.

Tannock GW, Munro K, Taylor C, Lawley B, Young W, Byrne B, Emery J, Louie T. 2010, "A new macrocyclic antibiotic, fidaxomicin (OPT-80), causes less alteration to the bowel microbiota of Clostridium difficile-infected patients than does vancomycin", Microbiology 156:3354-3359. doi:10.1099/mic.0.042010-0.

Li Y, Figler RA, Kolling G, Bracken TC, Rieger J, Stevenson RW, Linden J, Guerrant RL, Warren CA, "Adenosine A2A receptor activation reduces recurrence and mortality from Clostridium difficile infection in mice following vancomycin treatment", BMC Infect Dis. Dec. 10, 2012;12:342. doi: 10.1186/1471-2334-12-342.

Warren, CA, et al., "Vancomycin Treatment's Association with Delayed Intestinal Tissue Injury, Clostridial Overgrowth, and Recurrence of Clostridium Difficile Infection in Mice", Antimicrob. Agents Chemother. 2013, 57(2):689-96, Epub Nov. 12, 2012.

\* cited by examiner

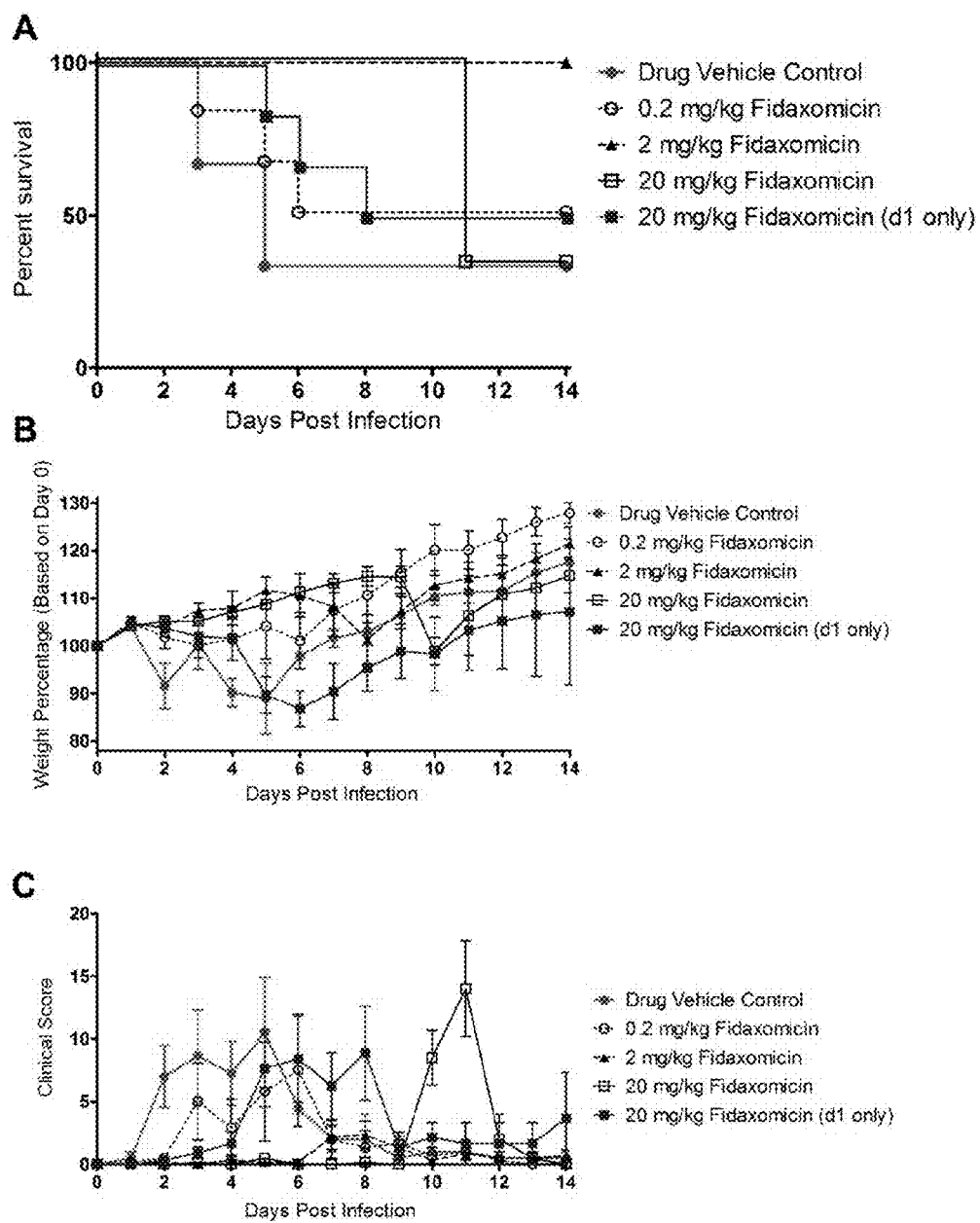
FIG. 11A-C

COMPOSITIONS AND METHODS FOR TREATING CLOSTRIDIUM INFECTION AND PREVENTING RECURRENCE OF INFECTION

CROSS REFERENCE TO RELATED APPLICATIONS

This application is entitled to priority pursuant to 35 U.S.C. §119(e) to U.S. provisional patent application No. 61/902,842, filed on Nov. 12, 2013. The entire disclosure of the afore-mentioned patent application is incorporated herein by reference.

STATEMENT REGARDING FEDERALLY SPONSORED RESEARCH OR DEVELOPMENT

This invention was made with government support under AI075526 and AI094458 awarded by the National Institute of Health. The government has certain rights in the invention.

BACKGROUND

*Clostridium difficile* infection (CDI) is a significant cause of antibiotic-associated nosocomial diarrhea. While discontinuation of the offending antibiotic is the ideal strategy to control the disease, in most cases, treatment with antimicrobial agents active against *C. difficile* is deemed necessary because of the severity of the gastrointestinal disease or the presence other active infections. Unfortunately, antimicrobial treatment for a first episode of CDI is associated with up to 25% recurrence of the disease (1).

After one incidence of recurrence, rates increase to up to 60% (2). A recurrence rate of up to almost 50% has been noted with metronidazole use (3). Even in the carrier state, it had been shown that treatment with either metronidazole or vancomycin of individuals with *C. difficile* is associated with the reisolation of the organism in the stool 2 months later, with recurrence not necessarily coming from the original strain (4). The recent epidemic saw the increasing failure of metronidazole to cure CDI (3, 5, 6). Vancomycin is now the drug of choice for severe disease (1, 7).

Fidaxomicin, a drug newly approved by the FDA, the European Medicines Agency, and Canada Health, is at least as effective as vancomycin in treating acute infection, but has been shown to have less recurrence (8). However, in infections due to NAP1/BI/027, the rates of recurrence in subjects treated with fidaxomicin and vancomycin were similar: 24.4% and 23.6%, respectively. Treatment of recurrent disease is problematic. For the first recurrence, a repetition of the regimen for the initial episode of CDI is recommended. Although there are no solid data for efficacy, prolonged and tapering or pulsed doses of vancomycin are the recommended strategy to treat a second recurrence (1). Even less evidence is available for alternative therapies for succeeding recurrences. Other antibiotics such as nitazoxanide and rifaximin, among others, had been considered (9, 10).

*C. difficile* infection is the most common cause of antibiotic-associated diarrhea. Unfortunately, antibiotic therapy remains as the standard treatment for this antibiotic-induced disease and relapses are common. Antibiotic treatment typically is given for 10 to 14 days for an initial or second episode of CDI ant at a dose of 2,000 mg/day or more. For recurrent episodes, more prolonged courses are recommended.

Alteration of the indigenous intestinal flora is critical to susceptibility to CDI and its recurrence. Antibiotic treatment may further disrupt the already abnormal flora and thereby enhance the growth of any leftover *C. difficile* organisms or of a newly acquired strain once antibiotics are discontinued.

There is a long felt need in the art for compositions and methods useful for treating *C. difficile* infection and for lowering the recurrence rate. The present invention satisfies theses needs.

SUMMARY OF THE INVENTION

Using a murine model of CDI, disclosed herein are the effects of vancomycin and alternative antibiotics such as fidaxomicin, metronidazole, and nitazoxanide, in treated mice versus controls with respect to clinical disease, relapse, mortality, intestinal histopathology, and fecal clostridial, toxin, and *Bacteroides* levels.

The present application discloses the unexpected result that lower doses or shorter courses of the antimicrobial treatment are sufficient to treat the infection and prevent or reduce recurrent disease by preserving the normal gut flora and immunologic response to infection and thus, protection against relapses or reinfection. In one aspect, the antimicrobial agent is vancomycin. The present invention further encompasses the use of other antibiotics at lower doses and for shorter periods of time where a similar result is obtained relative to vancomycin, including the drugs described herein and those known in the art.

The present application discloses that commonly used antibiotics such as vancomycin and fidaxomicin can be used at low doses and for short duration with better results than higher doses or longer duration, and that other antibiotics can be successful as well (data not shown). In one aspect, the method is useful for low dose treatment. In one aspect, the method is useful for short-term treatment. In one aspect, the compositions and methods of the invention are useful for both low dose and short-term treatment.

In one embodiment, the present invention provides compositions and methods useful preventing or treating a *Clostridium difficile* (*C. difficile*) infection, including re-infection, using a low dose of antibiotics. By low dose is meant a dose that is lower than what is typically prescribed by a physician. For example, some of the commonly used anti-*C. difficile* antibiotics are routinely administered in the art in doses much higher than those disclosed herein. The data disclosed herein show that in some instances an effective dose is an order of magnitude less than what is routinely used in the art. The present invention encompasses administrating to a subject a pharmaceutical composition comprising a low dose of at least one antibiotic effective against *C. difficile*. In one embodiment, doses less than 2.0 mg/kg/day are effective when administered. In one embodiment, depending on the particular antibiotic being administered and the route of administration, the dose ranges from about 0.1 mg/kg/day to about 20 mg/kg/day. In one embodiment, the dose is selected from the group consisting of 0.1, 0.5, 1.0, 1.5, 2.0, 2.5, 3.0, 3.5, 4.0, 4.5, 5.0, 6.0, 7.0, 8.0, 9.0, and 10.0, 11.0, 12.0, 13.0, 14.0, 15.0, 16.0, 17.0, 18.0, 19.0, and 20.0 mg/kg/day.

In one embodiment, duration of treatment is from about 1-10, 1-9, 1-8, 1-7, 1-6, 1-5, 1-4, 1-3, or 1-2 days. In one aspect, duration of treatment is from about 2-10, 2-9, 2-8, 2-7, 2-6, 2-5, 2-4, or 2-3 days. In one aspect, duration of treatment is from about 3-10, 3-9, 3-8, 3-7, 3-6, 3-5, or 3-4 days. In one aspect, duration of treatment is from about 4-10, 4-9, 4-8, 4-7, 4-6, or 4-5 days. In one aspect, duration of treatment is from about 5-10, 5-9, 5-8, 5-7, or 5-6 days. In one aspect, duration of treatment is from about 6-10, 6-9, 6-8, or 6-7 days. In one aspect, duration of treatment is from about 7-10, 7-9, or 7-8 days. In one aspect, duration of treatment is from about 8-10 or 8-9.

In one embodiment, treatment is for about 1, 2, 3, 4, 5, 6, 7, 8, 9, or 10 days.

In one embodiment, a subject is treated daily during the treatment regimen when the duration is longer than one day. In another aspect, the subject is treated every other day.

A compound of the invention can be administered once or more than once. It can be administered once a day or at least twice a day. In one aspect, a compound is administered every other day within a chosen term of treatment. In one embodiment, at least two compounds of the invention are used. In one aspect, a useful compound of the invention is selected from the group consisting of vancomycin, fidaxomicin, metronidazole, nitazoxanide, and rifaximin.

One of ordinary skill in the art can determine how often to administer a compound of the invention, the duration of treatment, and the dosage to be used. Factors used in such a determination include the severity of the infection, the age and health of the subject, the particular anti-*C. difficile* antibiotic being administered, and the route of administration.

It is disclosed herein that shorter course and lower doses of antimicrobial agents enable better immunologic responses and protection from relapse or reinfection, and likely also cause lesser alterations of the gut flora, reducing recurrent disease and ultimately, death from the infection. This strategy also cause less adverse events (toxicity from drugs) and is more economical.

The present invention includes the use of shorter courses of treatment than what are currently used in the art as the duration of choice, lower doses than what is currently the dose of choice in the art, and a combination of lower dose and shorter duration of treatment.

Treatment of CDI as described herein is useful for prevention of relapse or reinfection, as well as reducing the frequency of relapse or reinfection.

One of ordinary skill in the art can determine the dose and term of treatment to be used.

In one embodiment, for short durations of treatment the present invention provides a dosage range of at least one antibiotic of the invention of about 0.1 mg/kg to about 75 mg/kg. In one aspect, it is from about 0.5 to about 50 mg/kg. In another aspect, it is from about 2.0 to about 40 mg/kg. In yet another aspect, it is from about 3.0 to about 35 mg/kg. In another aspect, it is from about 4.0 to about 30 mg/kg. In a further aspect, it is from about 5.0 to about 25 mg/kg. In another aspect, it is from about 6.0 to about 20 mg/kg. In a further aspect, it is from about 7.0 to about 15 mg/kg. In one aspect, the dose is about 0.1, 0.5, 1.0, 2.0, 3.0, 4.0, 5.0, 6.0, 7.0, 8.0, 9.0, 10, 15, 20, 25, 30, 32, 35, 40, 45, 55, 60, 65, 70, or about 75 mg/kg. One of ordinary skill in the art can determine which dose to use depending on whether the treatment is for a short duration, or for a low dose, or a combination of the two. In one aspect, a short-term treatment such as 1 or 2 days may use a slightly higher dose than a treatment that lasts longer.

The total amount to be administered during a day can be divided into lower doses and administered at multiple times/day. In one aspect, the method is useful for low dose treatment. In one aspect, the method is useful for short-term treatment. For example, when 20 mg/kg/day is the prescribed amount for the day, that amount can be divided into more than one dose for administration during the day, such as doses of 10 mg/kg administered twice. In one embodiment, treatment can be as short as 1 day. Even doses as low as 0.1, 0.5, 1.0, 1.5, and 2.0 mg/kg/day can be administered as partial doses multiple times in a day when it is determined that the entire daily dose does not need to be administered in one bolus or that it would be better to administer the daily dose in several increments.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

An effective dose as described herein is, in one aspect, one that is sufficient to treat infection and control diarrhea and weight loss in a subject infected with *C. difficile*. Moreover, with this strategy, the intestinal gut flora is preserved and recurrent disease is prevented. Immunologic studies reveal that with standard doses of antibiotics, IgG production is reduced. It is disclosed herein that mice treated with low dose anti-*C. difficile* agents had higher IgG levels than those treated with high dose.

In one aspect, an effective dose reduces mortality.

In one aspect, the compositions and methods of the invention are useful for preventing relapse in an already treated subject and in preventing reinfection.

One of ordinary skill in the art can determine the best route of administration of a pharmaceutical composition of the invention. For example, administration can be direct, enteral, or parenteral. Enteral includes, for example, oral and rectal administration. Parenteral includes, for example, intravenous administration.

The present invention further encompasses the use of therapeutically active analogs and derivatives of the useful compounds of the invention. The structures of vancomycin and fidaxomicin are as follows:

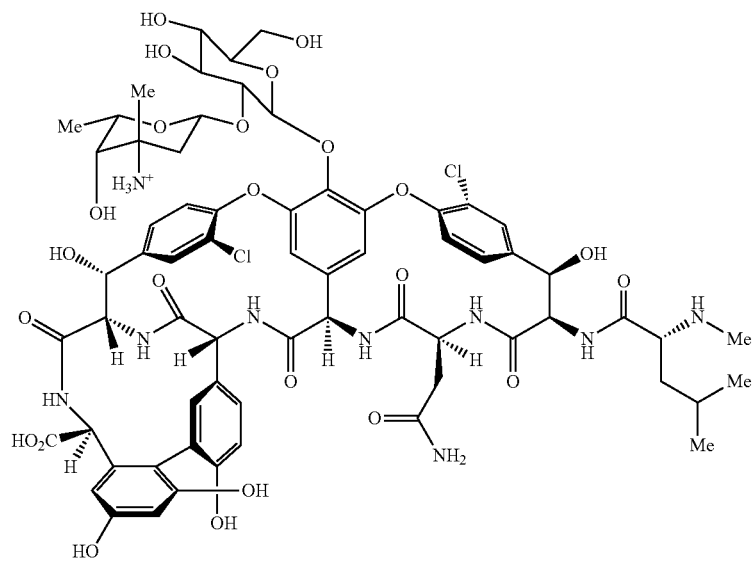

Vancomycin

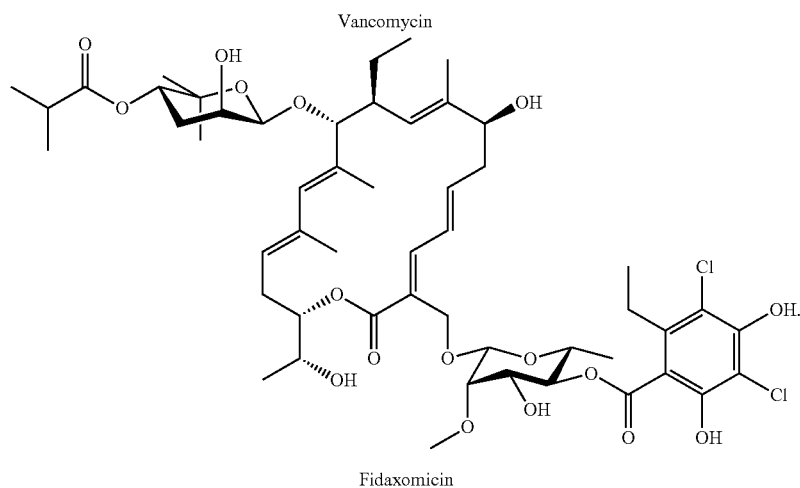

Fidaxomicin

The present invention therefore encompasses the use of biologically active analogs and derivatives vancomycin, fidaxomicin, metronidazole, nitazoxanide, and rifaximin, wherein the analogs and derivatives have the same biological activity and usefulness at low doses and/or short duration of treatment as disclosed herein for the parent compounds.

The present invention further provides for the use of a unit dose of a useful antibiotic, and biologically active analogs and derivatives thereof.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

In one embodiment, at least one antibiotic of the invention can be administered in conjunction with another therapeutic agent. Additional therapeutic agents include, for example, anti-diarrheals, steroids, anti-inflammatories, other antimicrobials, and inducers of chemokines. In one aspect, more than one therapeutic agent can be administered in conjunction with an antibiotic of the invention. Other antimicrobials include those drugs useful against infection other than a C. diff. infection where a subject may have need for treatment against an additional infection as well.

The present invention further provides kits comprising compounds of the invention, an applicator, and an instructional material for the use thereof.

Various aspects and embodiments of the invention are described in further detail below.

BRIEF DESCRIPTION OF THE DRAWINGS

FIG. 11A-C, comprising graphs A, B, and C, demonstrates the effect of low doses of fidaxomicin on survival of *C. difficile* infection, weight, and clinical score. A. Survival of animals in different drug treatment groups following infection, N=6 animals per group. Fourteen (14) day survival rates for each group were: Vehicle=33.3%, 0.2 mg/kg Fidaxomicin=50.0%, 2 mg/kg=100%, 20 mg/kg (5 days)=33.3%, and 20 mg/kg (1 day)=50.0%. A series of Log-rank tests comparing survival curves showed significantly increased survival of 2 mg/kg group compared with either the vehicle control (p=0.0191) or the 20 mg/kg/day group (p=0.0190), but not with the vehicle control compared to the 20 mg/kg/day group. In summary a lower dosage of Fidaxomicin significantly increased survival from infection compared with the drug vehicle and reduced relapse compared with a higher dosage (20 mg/kg). B. Weight change from baseline of animals in different drug treatment groups following infection. Each animal had its daily weight recorded, divided by their starting weight at infection, and multiplied by 100 to arrive at weight change from baseline. A two-way ANOVA did not find significant differences in weight across the course of the experiment; however you can see where infection starts to take hold or relapse occurs with weight drops in each group. C. Clinical scoring of animals in different drug treatment groups following infection. A two-way ANOVA performed between groups with Bonferroni correction post-test confirmed significantly less clinical scoring of mice receiving 2 mg/kg compared to mice receiving drug vehicle alone on days 3 and 5 post-infection (p<0.01), and significantly less clinical scoring of mice receiving 2 mg/kg/day compared with 20 mg/kg/day (5 days) on day 11 post-infection (p<0.001).

DETAILED DESCRIPTION

Figure 1:
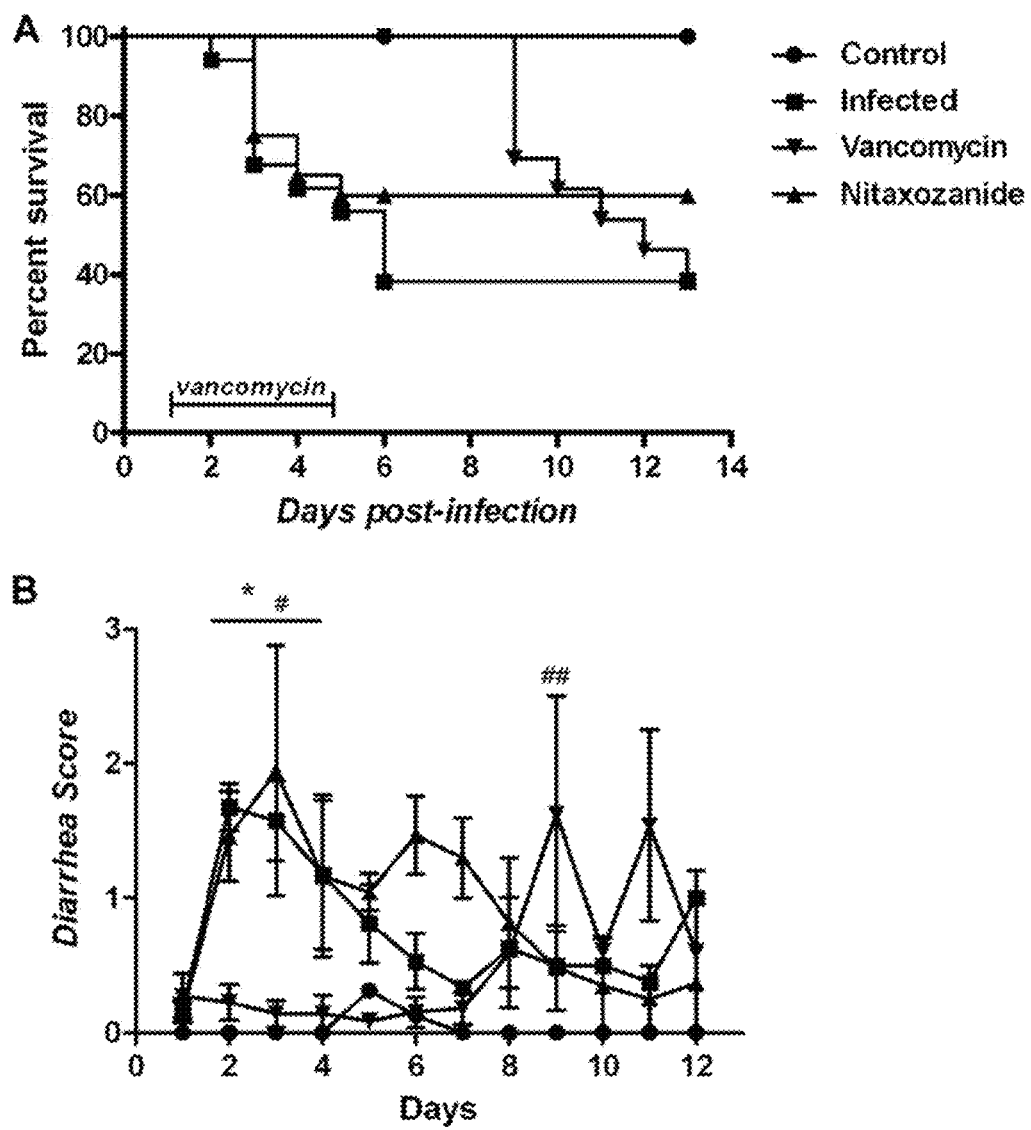
FIG. 1A-B: Effect of vancomycin on *Clostridium difficile*-infected mice during acute infection and posttreatment. C57BL/6 mice were inoculated with VPI 10463 at $10^4$ to $10^5$ by oral gavage on day 0. The results were data pooled from 94 mice from three 1-week-long and two 2-week-long experiments: 20 uninfected mice, 31 infected mice, 26 mice infected and treated with vancomycin, and 17 mice infected and treated with nitazoxanide. (A) Survival curve. P<0.0001 for uninfected versus infected mice, P=0.0064 for infected mice versus mice infected and treated with vancomycin, and P=NS for infected mice versus mice infected and treated with nitazoxanide by the log rank (Mantel-Cox) test. (B) Mean diarrhea scores. *, P<0.05 to 0.001 for uninfected versus infected mice; #, P<0.05 to 0.001 for infected mice versus mice infected and treated with vancomycin; and ##, P<0.05 for uninfected mice versus mice infected and treated with vancomycin; statistical significance was determined by two-way ANOVA with Bonferroni's correction.
Figure 2:
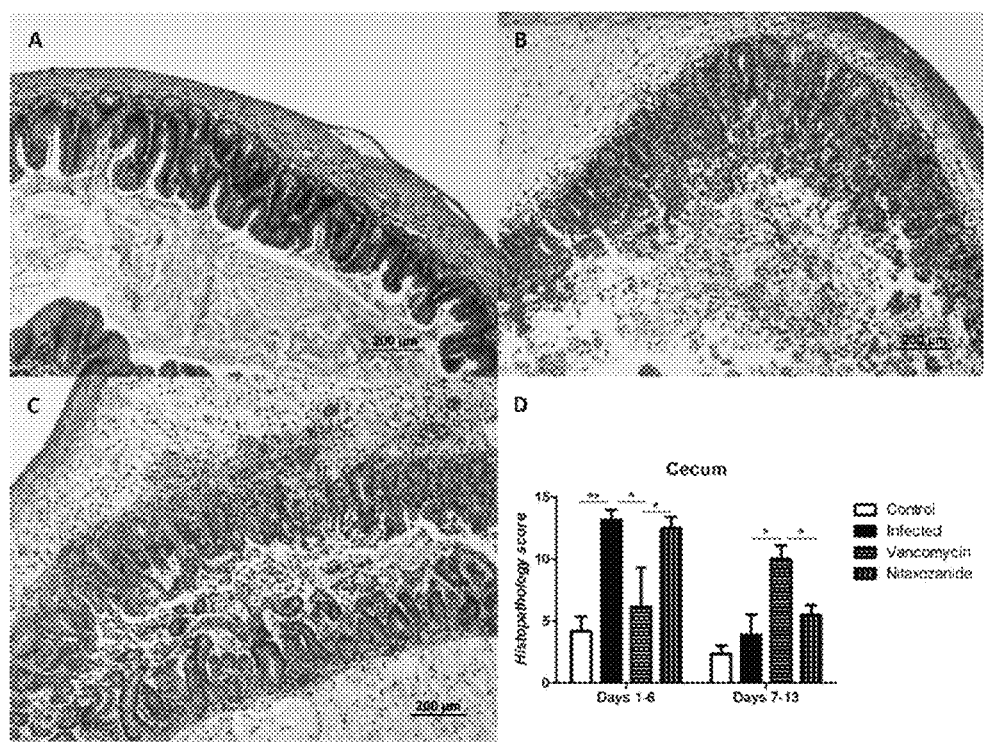
FIG. 2A-D: Intestinal histopathology. Shown are representative H&E-stained cecal tissues from infected mice treated or not with vancomycin for 5 days. (A) Uninfected control; (B) infected cecum at day 3; (C) vancomycin treated infection at day 9 (relapse); (D) histopathology scores of cecal tissues of uninfected mice (n=12), infected mice (n=16), mice infected and treated with vancomycin (n=15), and mice infected treated with nitazoxanide (n=16) moribund (at any day) or sacrificed (at the end of the experiment). *, P<0.01, and **, P<0.001, as determined by two-way ANOVA with Bonferroni's correction.

Abbreviations and Acronyms
CDI—*Clostridium difficile* infection
IgG—immunoglobulin G
I—infected
IC—infected control
kg—kilogram
mg—milligram
NS—not significant
OD—optical density
TcdA—*C. difficile* toxin A
TcdB—*C. difficile* toxin B
U—uninfected
UC—uninfected control

DEFINITIONS

As used herein, the terms below are defined by the following meanings:

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both. A "therapeutic" treatment is a treatment administered to a subject who exhibits signs of pathology for the purpose of diminishing or eliminating those signs.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

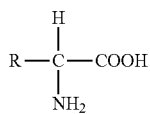

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin subunit molecules. The antibodies in the present invention may exist in a variety of forms including, for example, polyclonal antibodies, monoclonal antibodies, Fv, Fab and F(ab)2, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "secondary antibody" refers to an antibody that binds to the constant region of another antibody (the primary antibody).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "at least two antibiotics", as used herein, means at least two different antibiotics.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands. "Binding partner," as used herein, refers to a molecule capable of binding to another molecule.

The term "biological sample," as used herein, refers to samples obtained from a subject, including, but not limited to, skin, hair, tissue, blood, plasma, serum, cells, sweat, saliva, feces, tissue and/or urine.

As used herein, the term "biologically active fragments" or "bioactive fragment" of the polypeptides encompasses natural or synthetic portions of the full length protein that are capable of specific binding to their natural ligand or of performing the function of the protein. For example, a "functional" or "active" biological molecule is a biological molecule in a form in which it exhibits a property by which it is characterized. A functional enzyme, for example, is one which exhibits the characteristic catalytic activity by which the enzyme is characterized.

"Co-administer" can include simultaneous and/or sequential administration of two or more agents.

A "compound," as used herein, refers to any type of substance or agent that is can be considered a drug, or a candidate for use as a drug, as well as combinations and mixtures of the above.

The terms "comprises", "comprising", and the like can have the meaning ascribed to them in U.S. Patent Law and can mean "includes", "including" and the like. As used herein, "including" or "includes" or the like means including, without limitation.

As used herein, the term "conservative amino acid substitution" is defined herein as an amino acid exchange within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp "Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" generally means an amount which provides the desired local or systemic effect, such as enhanced performance. For example, an effective dose is an amount sufficient to affect a beneficial or desired clinical result. The dose could be administered in one or more administrations and can include any preselected amount. The precise determination of what would be considered an effective dose may be based on factors individual to each subject, including size, age, injury or disease being treated and amount of time since the injury occurred or the disease began. One skilled in the art, particularly a physician, would be able to determine what would constitute an effective dose.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide. The terms "fragment" and "segment" are used interchangeably herein. As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment" as applied to a nucleic acid, may ordinarily be at least about 20 nucleotides in length, typically, at least about 50 nucleotides, more typically, from about 50 to about 100 nucleotides, at least about 100 to about 200 nucleotides, at least about 200 nucleotides to about 300 nucleotides, at least about 300 to about 350, at least about 350 nucleotides to about 500 nucleotides, at least about 500 to about 600, at least about 600 nucleotides to about 620 nucleotides, at least about 620 to about 650, and or the nucleic acid fragment will be greater than about 650 nucleotides in length.

As used herein, "health care provider" includes either an individual or an institution that provides preventive, curative, promotional or rehabilitative health care services to a subject, such as a patient.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul [50; 1990]), modified as in Karlin and Altschul [51; 1993]. This algorithm is incorporated into the NBLAST and XBLAST programs of Altschul, et al. [52], and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. [53]. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide or antibody of the invention in the kit for diagnosing or effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "isolated" refers to a compound, including antibodies, nucleic acids or proteins/peptides, or cell that has been separated from at least one component which naturally accompanies it.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

"Pharmaceutically acceptable" means physiologically tolerable, for either human or veterinary application.

As used herein, "pharmaceutical compositions" include formulations for human and veterinary use.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "reduces recurrent infection" means that the number or percentage of subjects who get another *C. difficile* infection following a low dose or short-term course of treatment for an initial *C. difficile* infection is lower compared to the number who had received standard doses or standard duration therapies.

The term "regulate" refers to either stimulating or inhibiting a function or activity of interest.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker. Standard can also refer to a healthy individual.

A "subject" is a vertebrate, including a mammal, such as a human. Mammals include, but are not limited to, humans, farm animals, sport animals and pets.

The term "substantially pure" describes a compound, e.g., a protein or polypeptide, cell or nucleic acid that has been separated from components which naturally accompany it. Typically, a compound is substantially pure when at least 10%, including at least 20%, at least 50%, at least 60%, at least 75%, at least 90%, at least 95%, at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

As used herein, a "substantially homologous amino acid sequences" or "substantially identical amino acid sequences" includes those amino acid sequences which have at least about 92%, or at least about 95% homology or identity, including at least about 96% homology or identity, including at least about 97% homology or identity, including at least about 98% homology or identity, and at least about 99% or more homology or identity to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" or "substantially identical nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 92%, 95%, 99% or more. Substantial identity of nucleic acid sequences can be determined by comparing the sequence identity of two sequences, for example by physical/chemical methods (i.e., hybridization) or by sequence alignment via computer algorithm.

Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1×SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package. The default settings provided with these programs are suitable for determining substantial similarity of nucleic acid sequences for purposes of the present invention.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition. The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

Antimicrobials are substances that kill or inhibit the growth of microorganisms such as bacteria, fungi, virus or protozoans. Antimicrobial drugs either kill microbes (microbiocidal) or prevent the growth of microbes (microbiostatic).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. For example the, the active compound can be formulated so as to release only in the intestine and/or the colon.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds of invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary with the route of administration, the nature of the condition being treated and the age and condition of the patient and will be ultimately at the discretion of the attendant physician or clinician.

EXAMPLES

Example 1

The work described in Example 1 resulted in the publication of Warren et al., "Vancomycin treatment's association with delayed intestinal tissue injury, clostridial overgrowth, and recurrence of *Clostridium difficile* infection in mice", Antimicrob Agents Chemother. 2013, 57(2):689-96, Epub 2012 Nov. 12.

Materials and Methods

Example 1

Murine Model of *C. difficile* Infection and Treatment

The infection model is a modification of the published protocol of Chen et al. (11). This protocol has been approved by the Center for Comparative Medicine at University of Virginia. C57BL/6 mice, male, 8 weeks old, were used. From 6 to 4 days prior to infection, mice were given an antibiotic cocktail containing vancomycin (0.0045 mg/g), colistin (0.0042 mg/g), gentamicin (0.0035 mg/g), and metronidazole (0.0215 mg/g) in drinking water. One day prior to infection, clindamycin (32 mg/kg of body weight) was injected subcutaneously. The mice were divided into the following groups: control uninfected, control infected, infected and treated with vancomycin (20 mg/kg), and infected and treated with comparator drugs—nitazoxanide, fidaxomicin, and metronidazole (all drugs given at 20 mg/kg/day). Food and water were allowed ad libitum. Although each mouse or treatment group was housed in a separate cage, all mice were housed in the same pod of the vivarium. Infection was performed with VPI 10463 (ATCC) as an inoculum of $10^4$ or $10^5$ administered by oral gavage. This strain produces both *C. difficile* toxins A (TcdA) and B (TcdB). One day postinfection, treated mice were given either vancomycin or nitazoxanide at 20 mg/kg each by oral gavage daily for 5 days and monitored for either 1 or 2 weeks postinfection. One set of experiments was performed in which infected mice were treated with vancomycin (50 mg/kg) daily for 1, 2, 3, or 5 days and were observed for 21 days postinfection or with vancomycin (20 mg/kg) daily for either 5 or 10 days and monitoring for 15 days postinfection. In a separate experiment, mice given a preinfection antibiotic regimen described above were treated with either vancomycin, fidaxomicin, or metronidazole at 20 mg/kg/day for 5 days and infected another 5 days later. Except when indicated, all comparator drugs were administered using the same dosage (20 mg/kg/day for 5 days) to equally compare efficacies, outcomes, and effects on selected gut floras between treatment groups as previously described (12). From another study, a group of control mice was given vancomycin but was not infected. A clinical scoring system was developed on the basis of weight loss, diarrhea, activity level, and appearance of eyes and hair (each parameter scored from 0 to 3, where 0 is normal and 3 are the worst; maximum score of 20) (12). Stool specimens were collected daily. Diarrhea was scored as follows: 1 for soft or color change (yellow), 2 for wet tail or mucoid, and 3 for liquid or no stool (ileus). Mice judged moribund by the clinical score (score of >14) at any day and all surviving mice at the end of the experiment were sacrificed, and intestinal tissues and cecal contents were collected as described below. A separate set of experiments was performed for harvesting cecal contents for clostridial bacterial and toxin burdens at days 3, 6, 9, and 12 to 13 postinfection to follow changes at different time points of the study.

Histopathology.

Upon euthanasia, cecal and colonic tissues were fixed in 10% zinc formalin overnight and then placed in 10% ethanol before being sent for paraffin embedding and hematoxylin and eosin (H&E) staining at the University of Virginia Histology Research Core. Histopathologic scoring was performed coded (C.A.W. and M.S.R.). H&E-stained tissues were scored for mucosal disruption, mucosal hypertrophy, inflammation, vascular congestion and exudates, and submucosa edema (each parameter was graded from 0 to 3, with 0 as normal and 3 worst; maximum score of 15) as we previously described in detail (13).

Quantification of *C. difficile* and *Bacteroides*.

Genomic DNA was extracted from the stool or cecal samples using a modified protocol for the QIAamp DNA stool minikits (Qiagen). Stool lysis buffer (400 µl) was added to a frozen stool sample-diluent (from enzyme-linked immunosorbent assay [ELISA]) mixture. Samples were then vortexed for 15 s and incubated at 82.5° C. for 5 min. The samples were vortexed for another 15 s and then centrifuged at 14,000 rpm for 2 min. The supernatant was added to a clean 1.5-ml microcentrifuge tube. Thirty microliters of proteinase K was added to the wall of each tube, followed by 400 µl of lysis buffer. Samples were vortexed for 15 s and then incubated at 70° C. for 10 min. After incubation, 400 µl of 100% ethanol was added to each sample and then mixed by vortexing. A total of 650 µl of the sample was then added to a spin column provided in the kit and centrifuged at 14,000 rpm for 1 min. The remaining volume of each sample was then added to the spin column and centrifuged under the same conditions. The samples were washed first with 500 µl of AW1 buffer and centrifuged at 14,000 rpm for 1 min and then with 500 µl of AW2 buffer and centrifuged at 14,000 rpm for 3 min. The DNA was eluted by adding 200 µl of elution buffer to the spin column and then centrifuging at 14,000 rpm for 1 min. All quantitative PCRs (qPCRs) were performed on the Bio-Rad iCycler using primers to detect the toxin B (tcdB) gene or gene sequence common to *Bacteroides* spp. (14). Mixtures for qPCRs, in a final volume of 20 µl, consisted of 10 µl of QuantiFast SYBR green Supermix (Qiagen), 1 µl each of forward and reverse primers, 4 µl of sterile water, and 4 µl of sample DNA. PCR assays were performed in duplicate under the following cycling conditions: 3 min at 95° C., 10 s at 95° C., and 30 s at 57° C. (59° C. for *Bacteroides*) for 40 repeats and a melt curve between 65° C. and 95° C. of 5 s at 0.5° C. intervals. For both *C. difficile* and *Bacteroides* spp., standard curves were generated from known concentrations of bacteria grown under anaerobic conditions. Bacterial counts were expressed as counts or colonies per mg of mouse stool assayed.

*C. difficile* Toxin Assay.

*C. difficile* toxins A and B were detected using a modified protocol for the Tech Lab Toxin A/B II ELISA kit. Each stool sample was weighed and the amount of diluent per sample was normalized to provide the same stool mass-to-diluent ratio for each sample. The diluent-sample mixtures were homogenized by grinding and vortexing, and 1:10, 1:100, and 1:1,000 serial dilutions were made of the sample. A total of 150 µl of the 1:1,000 dilution of each sample was added to a precoated well provided in the kit. A negative control consisted of 150 µl of diluent, and a positive control consisted of 135 µl of diluent plus 3 drops of the positive control toxin A-B mixture provided in the kit. One drop of conjugate was added to each well, and the plate was incubated at 37° C. for 50 min. Each well was washed three times with 150 µl of a 1× dilution of the wash buffer provided in the kit. Two drops of substrate were added to each well. After 10 min, 1 drop of stop solution was added to each well. The plate was allowed to sit for 2 min before being read in an ELISA reader.

Statistical Analysis.

Results were expressed as means±standard errors of the means (SEM), as generated by GraphPad Prism, version 5.0 (GraphPad Software, San Diego, Calif.). The differences between experimental groups were compared using analysis of variance (ANOVA) with Bonferroni's multiple-comparison test. Two-way ANOVA was used to compare experimental groups across time periods. If needed, differences between 2 groups were analyzed using unpaired Student's t test. Mortality rates between treatment groups were analyzed with the log rank (Mantel-Cox) test or the log rank test for trend. Statistical significance was set at a P value of <0.05.

Results

Example 1

Effects of Vancomycin on Acute CDI (1st Week Postinfection)

Mice infected with VPI 10463 showed clinical symptoms 2 days after inoculation with the bacteria by gastric gavage. Clinical disease scores, weight loss, and diarrhea, among other parameters, were noted to increase at day 2 (FIG. 1B). Vancomycin treatment of infected mice was associated with improved mean clinical score versus that for infected controls (1.7±0.3 versus 5.7±0.9; P<0.01), while no difference was seen in nitazoxanide-treated mice (5±1 versus 5.7±0.9) in the first week after infection. Likewise, weights in infected mice were minimally affected by vancomycin treatment. Infected mice which started treatment with vancomycin 1 day after inoculation remained relatively well, almost similar to uninfected control mice, during treatment. In comparison, the infected group treated with nitazoxanide had deaths between days 2 and 6, similar to the infected control group. Untreated infected mice had an overall survival rate of 38% in this study, and vancomycin prevented 100% of these deaths during the acute infection period (FIG. 1A). Nitazoxanide was able to prevent deaths in infected mice by 60% only.

Effects of Vancomycin Treatment after Acute CDI (2nd Week Postinfection)

Infected mice which did not receive antimicrobial treatment but survived acute infection (first week postinfection) were able to recover almost completely during the second week of the study (FIG. 1A-B). No additional deaths occurred during the post-acute infection period. Likewise, infected mice treated with nitazoxanide continued to recover, and no additional deaths were noted. Interestingly, vancomycin-treated mice started exhibiting signs of infection a few days after the last dose of the drug was given. The mean clinical scores in the second week postinfection were worse for vancomycin-treated mice than for surviving untreated infected mice (6.2±0.2 versus 2.6; P<0.001). Clinical scores worsened, weight loss was observed, and deaths (62%) occurred by day 9 and onwards in the vancomycin-treated group.

Figure 7:
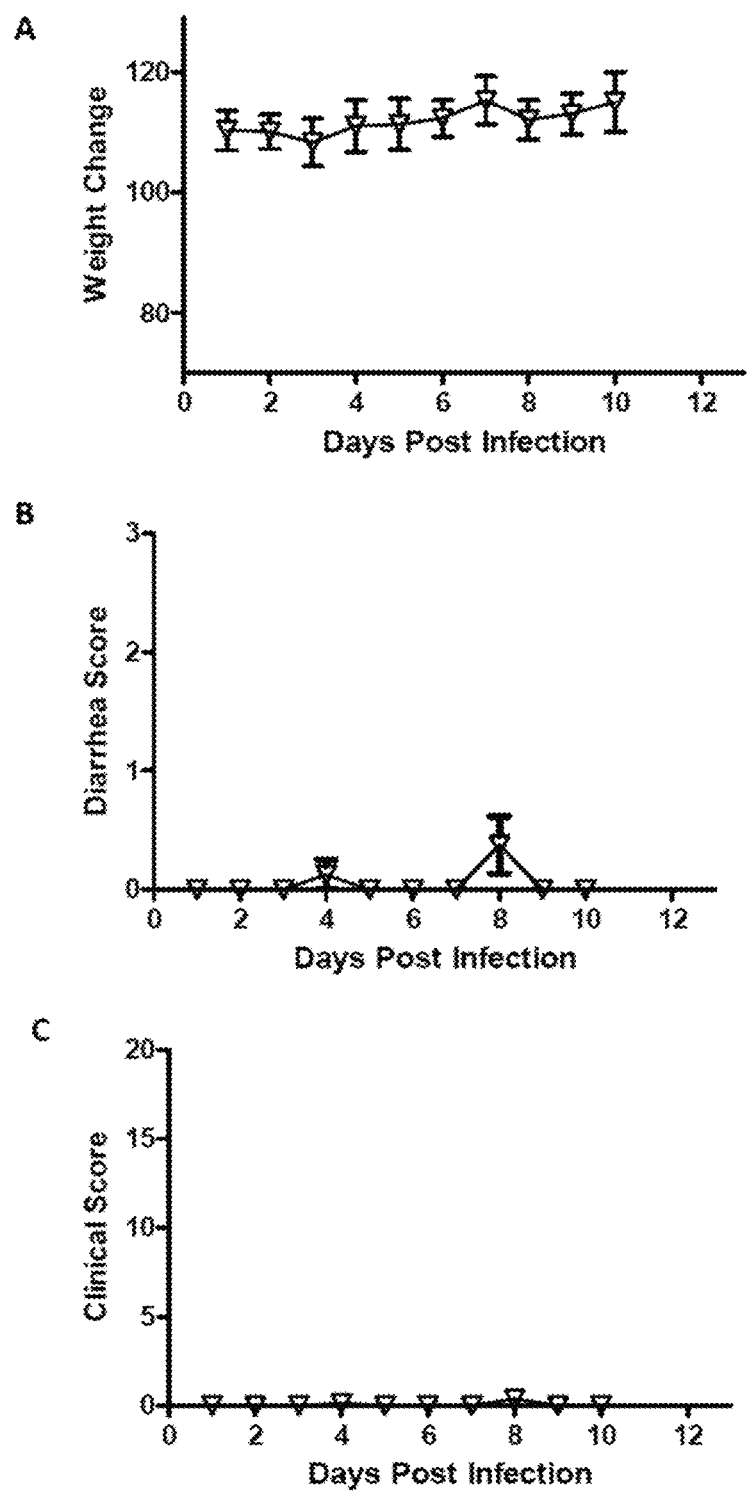
FIG. 7A-C: Effect of vancomycin treatment in uninfected mice (n=4) on weight and diarrhea and clinical scores.

Of note, in a separate study, uninfected mice treated with a 5-day course of vancomycin alone did not show weight loss or an increase in disease score (see FIG. 7A-C).

Histopathologic Changes During and after Acute CDI.

To investigate further the underlying changes that infection and antibiotic treatment cause at the site of infection, we pooled the histopathologic scores of cecal and colonic tissues from moribund mice during the acute infection period of the study (1st week postinoculation) and compared these with the scores of tissues collected after acute infection (2nd week postinoculation). In one experiment, intestinal tissues from 3 mice each from the uninfected control and vancomycin treatment groups were collected at day 3 (peak of infection) for comparison with the others at the 1st week. As expected, in the first week, untreated infected mice had the worst histopathology (12.5±0.7), followed by nitazoxanide-treated mice (11.53±0.9). Only minimal intestinal tissue changes were seen in vancomycin-treated infected mice (4.5±1.6 versus 2.2±1 in uninfected control mice; P value, not significant [NS]) at the peak of infection. By the second week of observation, infected control mice had near-normal intestinal tissue morphology, similar to that of uninfected control mice (2.7±0.9 versus 1.6±0.26, respectively). In contrast, vancomycin-treated mice had significantly worse histopathology scores than infected control mice (9.3±0.9 versus 2.7±0.9, respectively; P<0.001) in this period. Compared to the elevated score (11.53±0.9) in the first week, nitazoxanide-treated mice showed improved histopathology by the 2nd week, with scores (4.2±0.6) now not significantly different from those of the uninfected controls (1.6±0.26). FIG. 2A-D shows representative H&E-stained sections and histopathologic scores of cecal tissues from the different treatment groups.

Fecal Burden of Clostridial Infection and Toxin Posttreatment.

Figure 3:
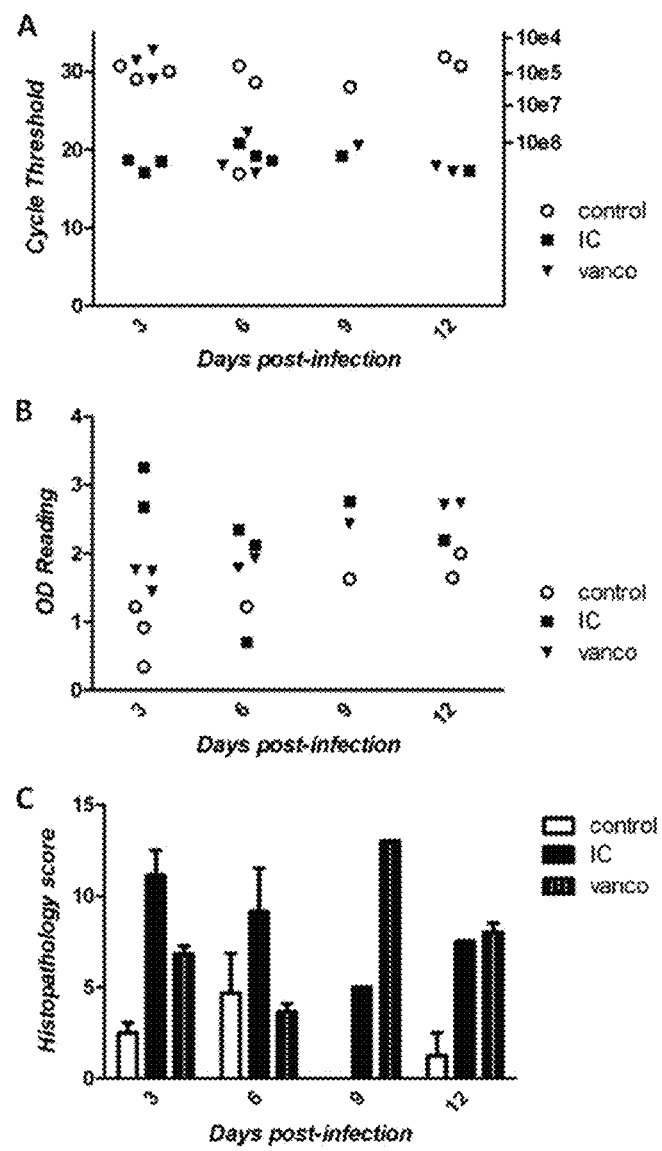
FIG. 3A-C: Clostridial and toxin burdens in cecal contents at peak of infection, post-vancomycin treatment, and at relapse. Mice were infected with VPI 10463 ($10^5$) and treated (vanc; n=9) or not (infected control [IC]; n=9) with vancomycin. The uninfected group (control) had 9 mice also. Cecal contents and tissues were collected at days 3 (peak of infection), 6 (postvancomycin), 9 (relapse), and 12 (end of experiment). (A) Cecal tcdB shedding; (B) TcdA and TcdB levels in cecal contents; (C) histopathology scores.

To determine whether the delayed histopathologic changes and increased mortality were associated with increased clostridial burden, we evaluated the presence of the C. difficile gene tcdB in cecal specimens from mice treated or not with vancomycin at the peak of infection (day 3), post-vancomycin treatment (day 6), at relapse (day 9), and at the end of the experiment (day 12). C. difficile DNA (tcdB) and toxin levels in the vancomycin-treated group were low, almost similar to those in the uninfected group on day 3 (FIGS. 3A and 3B). At day 6 (1 day after antibiotic was discontinued), increased clostridial burden was noted in the treatment group, which persisted on days 9 and 12. Similarly, toxin levels were lower on day 3 but increased progressively at the succeeding time points. Consistent with their initial low bacterial and toxin levels, vancomycin-treated mice sacrificed at day 3 had reduced histopathology scores compared with those of infected controls (FIG. 3C). Of note, all mice (including uninfected controls) underwent preinfection antibiotic cocktail treatment. Uninfected mice, even without overt disease, were observed to shed tcdB and/or TcdB.

Effects of Duration of Vancomycin Treatment on Clinical Disease and Histopathology.

Figure 4:
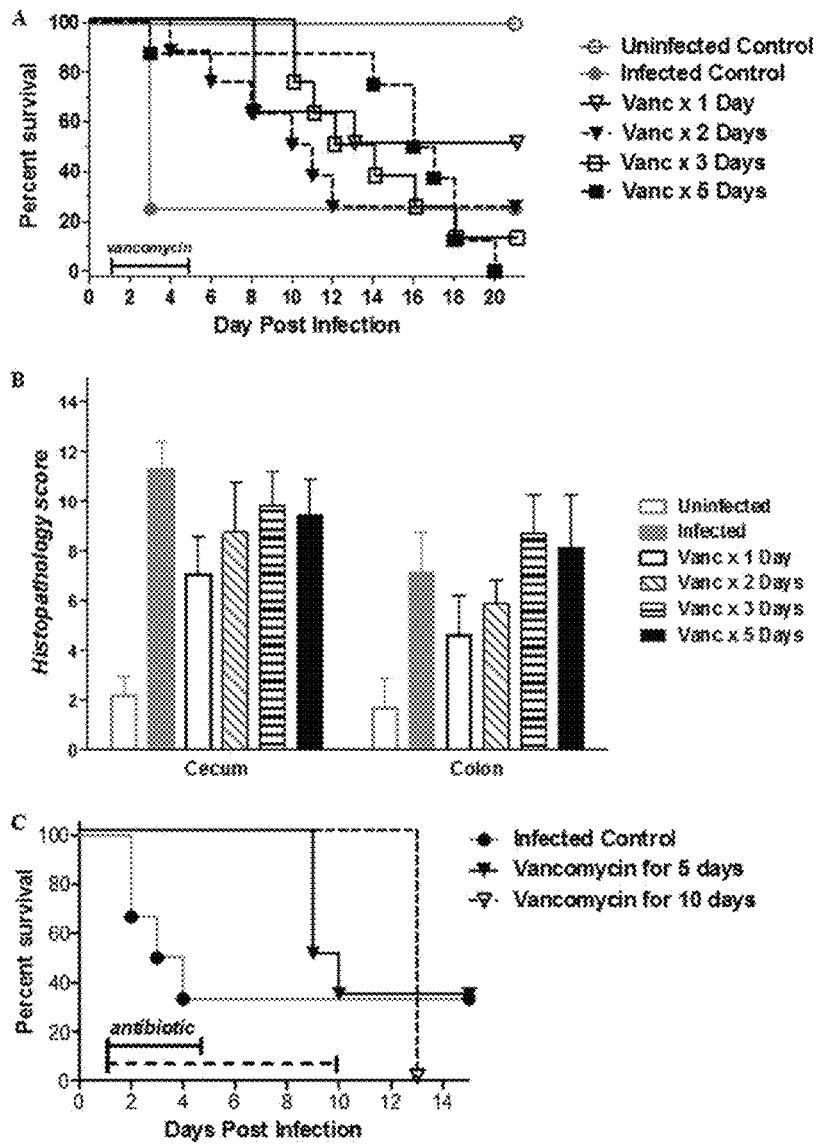
FIG. 4A-C: Effect of duration of vancomycin treatment on disease and survival in mice with CDI. For panels A and B, mice were infected with VPI 10463 ($10^5$) and treated or not with vancomycin (50 mg) given for 1, 2, 3, or 5 days. Each treatment group, including uninfected and infected controls, had 8 mice each. For panel C, infected mice were treated with vancomycin (20 mg) given for either 5 days or 10 days. Each treatment group had 6 mice. (A) Survival curve. P=0.026 by log rank test for trend; P=0.004 for infected versus uninfected mice and P=0.092 for infected controls versus mice treated with vancomycin for 1 day by log rank (Mantel-Cox) test. (B) Histopathology scores of colonic and cecal tissues at time of sacrifice and/or at the end of the observation period. (C) Survival curve. P=0.3790 by log rank test for trend.

To evaluate if the survival from CDI correlated with the length of exposure to vancomycin, various durations (1, 2, 3, and 5 days) of treatment were tested in the mouse model. In this study, we used 50 mg, instead of 20 mg, of vancomycin to indirectly assess the effect of a higher dose of the drug on CDI. Vancomycin at 50 mg, given for 5 days, had an overall mortality rate of 100%, compared to 75% in infected controls (FIGS. 4A-C). As the duration of treatment was progressively decreased from 5 days to 1 day, survival from CDI increased. As observed in weights, clinical scores, and diarrhea scores, the advantage of vancomycin was consistently evident only during treatment of acute infection; weights decreased and scores worsened few days after discontinuation of vancomycin. The least weight loss and best clinical outcomes were noted in the group that was treated with the vancomycin for 1 day only. Combined histopathologic scores (regardless of day of tissue harvest) showed a trend of decreased intestinal injury in 1- and 2-day versus 3- and 5-day courses, although these differences were not statistically significant (FIG. 4B).

Next, we compared the outcomes in infected mice treated with vancomycin (20 mg/kg/day) given for 5 and 10 days. Consistent with what is described above, relapse from the 5-day treatment course occurred 4 days later (FIG. 4C). Interestingly, the 10-day treatment course resulted to earlier relapse—3 days after discontinuation of the antibiotic—and a higher mortality rate. In both treatment groups, weights were stable and the clinical score was <1 until recurrence of disease.

Outcome of Infection in Mice Treated with or Exposed to Vancomycin, Fidaxomicin, or Metronidazole.

Figure 5:
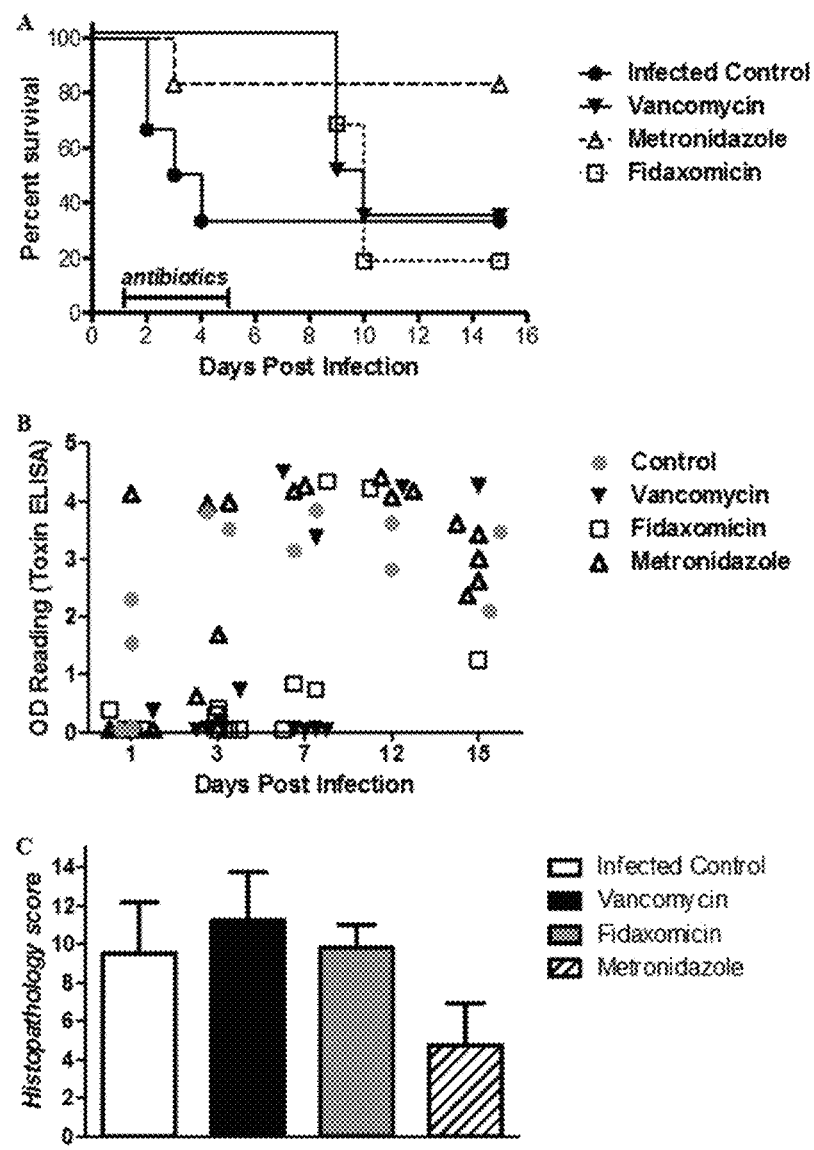
FIG. 5A-C: Effect of vancomycin, fidaxomicin, or metronidazole on *Clostridium difficile*-infected mice during acute infection and posttreatment. C57BL/6 mice were inoculated with VPI 10463 at $10^5$ by oral gavage on day 0. Anti-*C. difficile* drugs (20 mg/kg/day) were given from days 1 to 5. Each group had 6 mice. (A) Survival curve. P=0.42 by log rank test for trend. (B) Fecal TcdA and TcdB levels. OD, optical density. (C) Histopathology scores from sacrificed moribund mice (at any day) and surviving mice (at the end of the study). P=0.36 by one-way ANOVA.

We compared infected mice treated with vancomycin to those treated with either fidaxomicin or metronidazole, with all antibiotics given at 20 mg/kg/day for 5 days. Compared to untreated infected mice and similar to mice treated with vancomycin, mice that received fidaxomicin did not have weight loss or diarrhea while on antibiotics (see FIGS. 8A-B), but almost all eventually succumbed to the disease a few days after treatment (FIG. 5A). Metronidazole-treated mice had diarrhea and weight loss during treatment, although to a lesser degree than infected controls. During treatment, one mouse from the metronidazole-treated group, versus none from other treated groups, died of infection. However, while most of the infected mice treated with vancomycin (67%) or fidaxomicin (83%) relapsed, none of the metronidazole-treated or untreated infected controls had a recurrence of the disease. Bacterial, toxin shedding, and histopathology scores are shown in FIGS. 5B-C.

Figure 6:
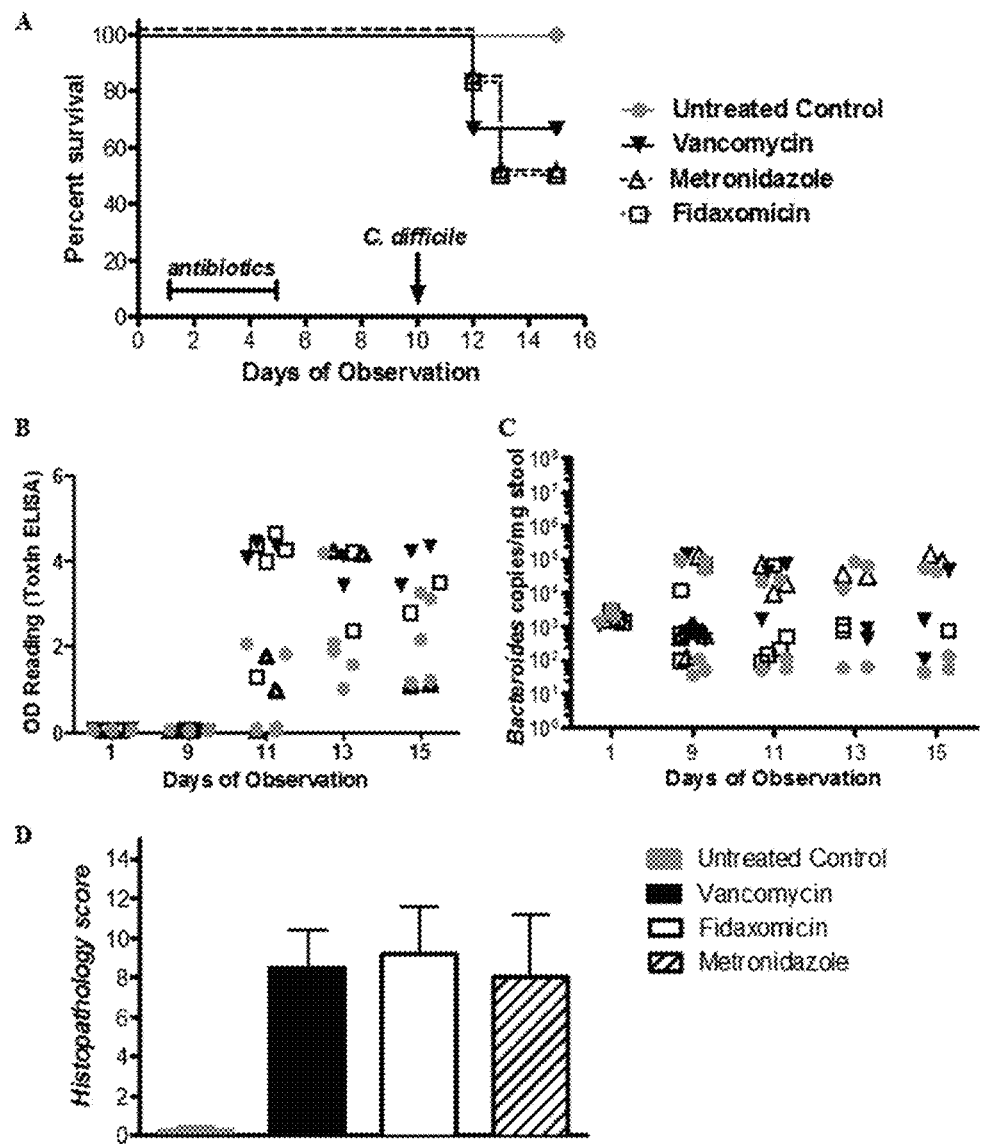
FIG. 6A-D: Effect of preexposure to vancomycin, fidaxomicin, or metronidazole on *C. difficile*-infected mice. All mice were pretreated with an antibiotic cocktail from day −6 to day −1 (described in the text), then given anti-*C. difficile* drugs (20 mg/kg/day) or not (untreated control) from days 1 to 5, and then infected with VPI 10463 at day 10. Each treatment group had 6 mice. (A) Survival curve. P=0.11 by log rank test for trend. (B) Fecal TcdA and TcdB levels by ELISA. (C) Fecal *Bacteroides* levels by PCR. (D) Histopathology scores. P=0.03 by one-way ANOVA.
Figure 8:
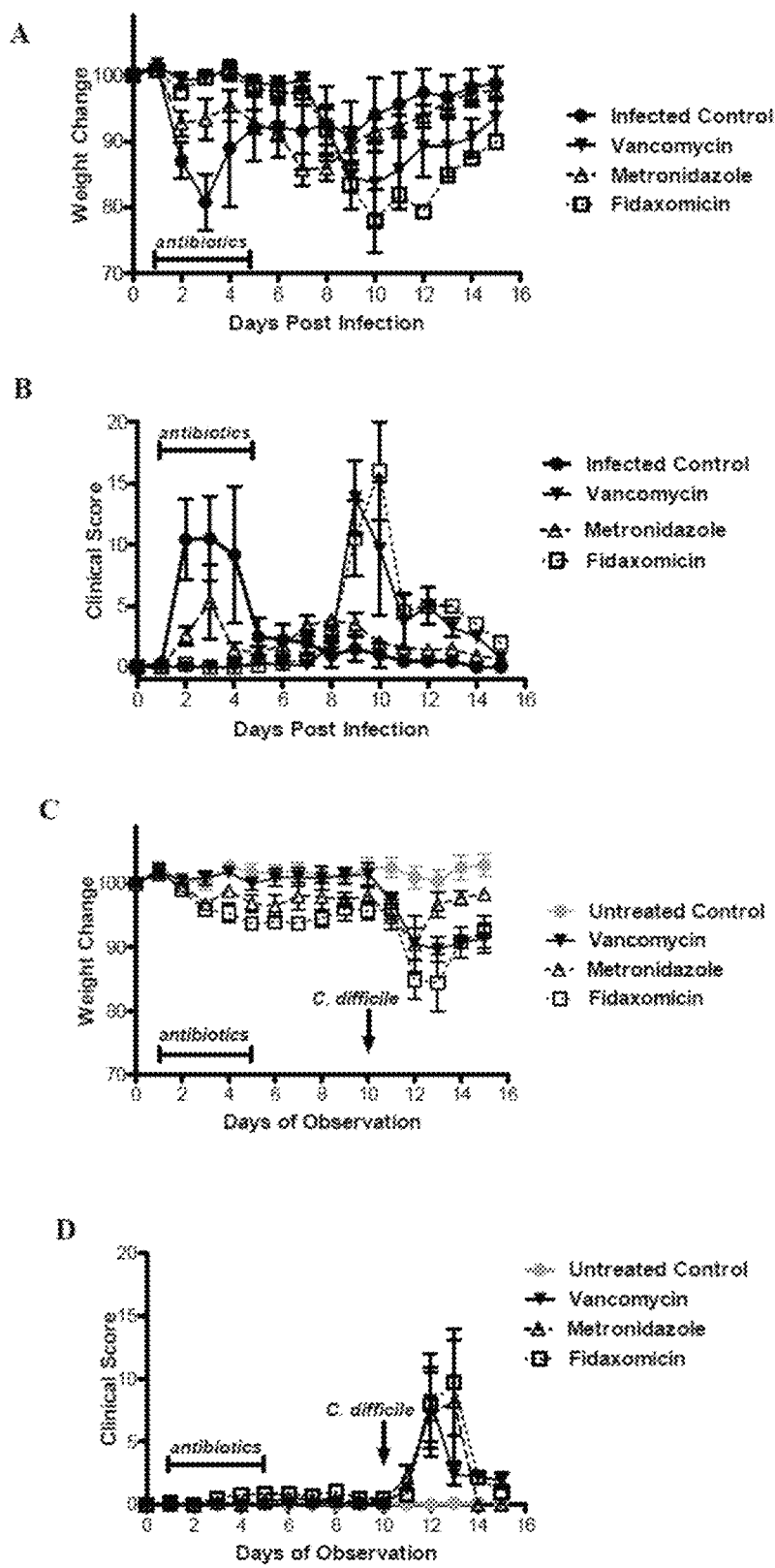
FIG. 8A-D: Weights and clinical scores in *C. difficile*-infected mice treated (Panels A & B) or pre-exposed (Panels C & D) to vancomycin, fidaxomicin, or metronidazole. All drugs were at 20 mg/kg/day. Each group had 6 mice.
Figure 9:
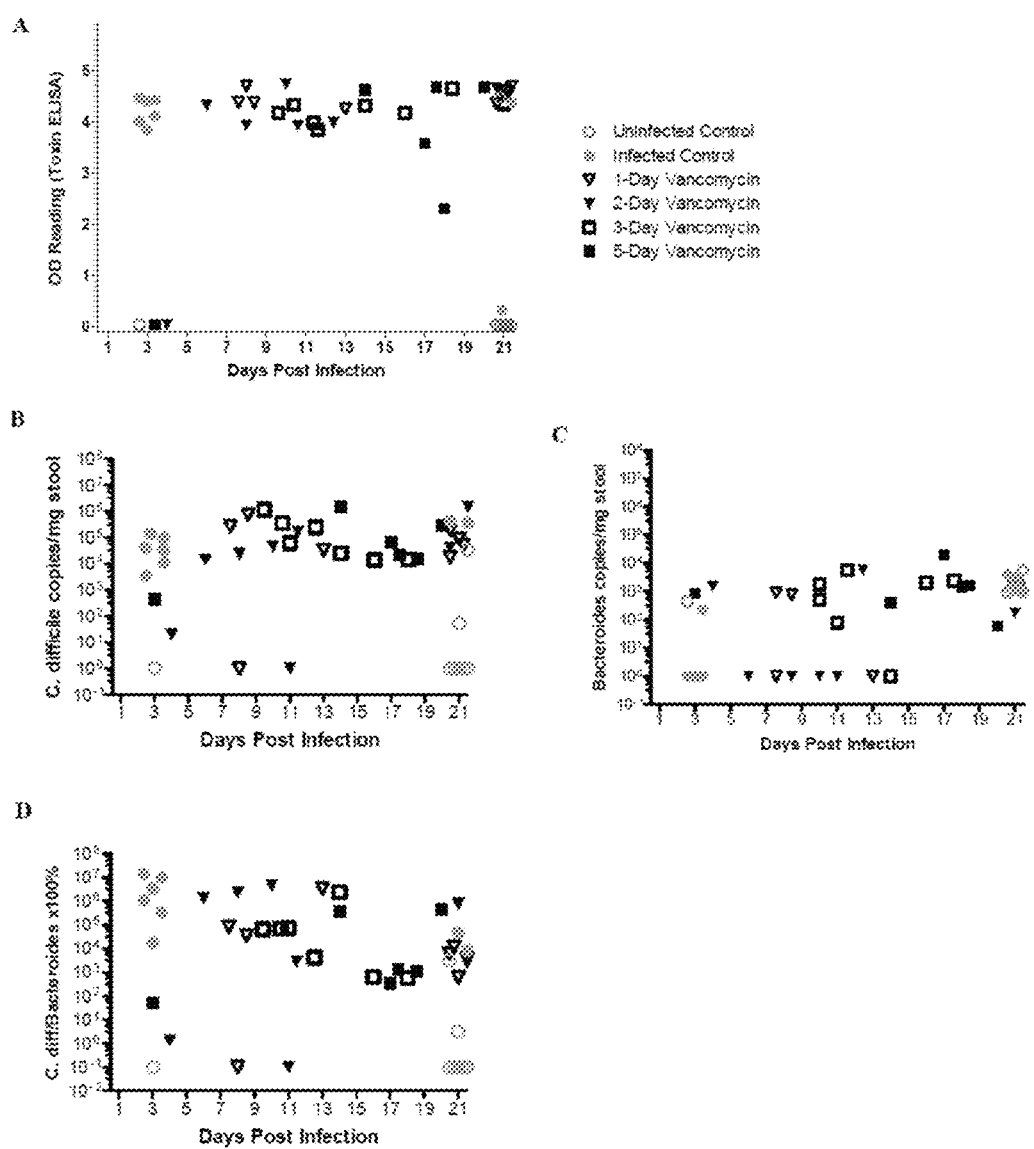
FIG. 9A-D: Effect of duration of vancomycin treatment on cecal levels of clostridial bacteria, toxin, and *Bacteroides*. Mice were infected with VPI10463 ($10^5$) and treated or not with vancomycin (50 mg) given for either 1 (V1), 2 (V2), 3 (V3) or 5 (V5) days. Number of available cecal contents per group: Uninfected (U) control, 7; infected (I) control, 8; V1, 8; V2, 8; V3, 7; V5, 6. Cecal contents from mice found dead (not euthanized) were excluded.

To determine the effects of the anti-*C. difficile* drugs on uninfected mice and their predisposition to a later infection, uninfected mice were exposed to vancomycin, fidaxomicin, or metronidazole prior to infection. Except for mild weight loss (<10%) in mice treated with fidaxomicin and metronidazole, the overall disease scores in all treatment and untreated control groups were similar prior to infection (FIGS. 8C-D). Upon infection, mice previously exposed to the antibiotics developed disease, whereas none of the untreated controls did. All antibiotic-treated groups were equally susceptible to death from infection (FIG. 6A).

Effects of Anti-*C. difficile* Treatment on Cecal Clostridial Burden and Anaerobes.

Given that antibiotic treatment during CDI was associated with relapses and that exposure to anti-*C. difficile* drugs predisposed to a later infection, we then investigated whether cecal clostridial burden and toxin levels or the anaerobic bacterial community would also be altered by the treatment. *Bacteroides* spp. are the most common anaerobes in the gut and were therefore chosen to represent the anaerobic flora other than *C. difficile* (15). The amounts of clostridial DNA and toxin from the cecal contents of infected mice that received vancomycin were similar to those in untreated infected mice (FIGS. 9A-D). All groups had uniformly low levels of *Bacteroides* ($10^2$ to $10^4$/mg of stool). Except for uninfected controls, all infected mice had overgrowth of *C. difficile* in their cecal contents as measured by the *C. difficile/Bacteroides* ratio. Antibiotic treatment of uninfected mice variably affected the anaerobic community in the treated group (FIG. 6C). Untreated controls, although showing an alteration in gut *Bacteroides* spp. similar to those in treated groups, when infected with the same amount of *C. difficile* did not develop disease (FIGS. 8C-D) and had normal histology at the end of the observation period (FIG. 6D).

Discussion

Example 1

Vancomycin is the current drug of choice for severe CDI (1). In this report, we have demonstrated that while vancomycin was effective in controlling acute infection, the antibiotic-treated infected mice were highly susceptible to severe disease of a later onset, resulting in overall mortality rates at least similar to those of untreated infected controls. In the mouse infection model, vancomycin was not able to completely eradicate *C. difficile* bacterial and toxin shedding, thus perpetuating clostridial predominance over the commensal anaerobes in the intestinal lumen. Moreover, we confirmed that fidaxomicin-treated mice had outcomes similar to those of vancomycin-infected mice.

In humans, vancomycin had been shown to be more effective than metronidazole in treating severe disease (7). Other newer antibiotics also claim efficacy against CDI (8-10, 16-18). However, recurrence of CDI after an initial successful treatment with antibiotics occurs in 24%, and the rate increases to 65% in those patients with a history of a prior recurrence (19). In our animal study, both vancomycin and fidaxomicin were able to control disease during treatment but were uniformly ineffective in preventing recurrent disease. Similar observations with vancomycin had been reported by others (11, 20). Mechanisms underlying recurrent disease remain unclear. Inability to eradicate spores may lead to a later recrudescence when the anti-*C. difficile* agents are stopped. While highly active against vegetative bacteria in vitro (21), vancomycin was shown to have no antispore activity (22), and although fidaxomicin was reported to inhibit sporulation (23), its activity against preexisting spores is unproven. Second, inadequate suppression of toxin production may also contribute to recurrence of disease. Clinical studies have shown that individuals that had a robust anti-*C. difficile* toxin A (TcdA) or B (TcdB) response were less susceptible to symptomatic infection and experienced fewer reinfections (24, 25). The use of monoclonal antibodies against TcdA and TcdB, after standard antibiotic treatment, was shown to be effective in reducing recurrences (26). The toxin binder tolevamer, although inferior to comparator drugs in treating acute infection, was also associated with significantly less recurrence (27). Failure to completely suppress toxin production in situ (as fecal levels of TcdA and TcdB were actually depressed in treated mice) by either vancomycin or fidaxomicin may partially explain recrudescence of the disease.

Inadvertent inhibition and delay of recovery of gut anaerobes and other beneficial floras because of further antibiotic use may also increase susceptibility to relapse or reinfection. In contrast to antibiotic-treated mice, untreated infected mice that survived acute infection recovered completely, suggesting eventual intestinal mucosal recovery in the absence of antibiotics if acute infection is overcome. These observations suggest that anti-*C. difficile* treatment may only delay recovery of the intestinal flora, which is essential in preventing the overgrowth of the pathogen. One study has evaluated the effects of vancomycin in the intestinal microbiotas of 10 individuals pretreated with cefuroxime (28). In these subjects, vancomycin treatment caused decreases in *Enterococcus* and anaerobes, including *Bifidobacterium* and *Bacteroides* species. *Enterococcus* with decreased susceptibility or resistant to vancomycin and other vancomycin-resistant strains of *Pediococcus*, *Lactobacillus*, and various Gram-negative organisms emerged. Interestingly, although not as effective in treating acute infection, nitazoxanide and metronidazole were associated with relapse to a lesser degree.

We have previously reported that nitazoxanide and its novel derivative amixicile selectively inhibit pyruvate-ferredoxin oxidoreductase in anaerobic bacteria, possibly sparing beneficial bacteria such as *Lactobacillus* spp., *Bifidobacterium*, and Enterobacteriaceae that lack this drug target (12). On the other hand, metronidazole has a very broad spectrum of anaerobic coverage. However, its activity against certain beneficial floras may be species and dose dependent. In this study, we used the same dosage (20 mg/kg/day) for all comparator drugs as previously published (12). Although found to be effective against infection, this dose of metronidazole may be lower than those of the other drugs relative to what is given in human disease and probably, did not have the same effect in the gut flora, resulting in less recurrence. The newly FDA-approved drug fidaxomicin was reported to cause less disruption of the gut flora in infected patients than vancomycin (29, 30). It apparently spared *Bacteroides* species and affected less of clostridial clusters XIVa and IV and *Bifidobacterium* during treatment for CDI. It has been shown to be at least non-inferior to vancomycin in treating CDI and was associated with significantly lower rates of recurrence, but only in non-NAP1 strains (8). However, similar to what was observed in clinical trials in individuals infected with NAP1, we demonstrated that the rates and severity of recurrence in mice treated with fidaxomicin resembled those of vancomycin-treated mice. Thus, it appears that while the gut microbiome may be essential, antibiotic-induced alteration in several other factors, such as host and bacterial factors, are probably also significantly involved in the development of recurrent CDI. Moreover, other non-*Bacteroides* members of the gut flora, that are susceptible to vancomycin or fidaxomicin, may play a more critical role in controlling infection. That decreasing the duration of treatment with vancomycin reduced recurrence and improved survival in treated mice confirms that further exposure to antibiotics, even agents active against *C. difficile*, is detrimental to this antibiotic-induced disease.

At present, the use of drugs active against *C. difficile* is critical in controlling moderate to severe infection. In our study, we demonstrated that vancomycin, while very effective in treating acute CDI in the mouse model, is associated with persistent predominance of toxigenic *C. difficile* over *Bacteroides* in the gut and recurrence of severe disease post-treatment. Decreasing the dose and duration of vancomycin treatment, as disclosed herein, actually improved overall survival and prevented recurrences in infected mice. These findings suggest that limited antibiotic exposure may be sufficient to control the disease and may actually improve outcomes. Investigating the optimal duration of antimicrobial treatment for CDI and employing adjunctive therapies that limit the use of antibiotics would be ideal.

Example 2

Figure 10:
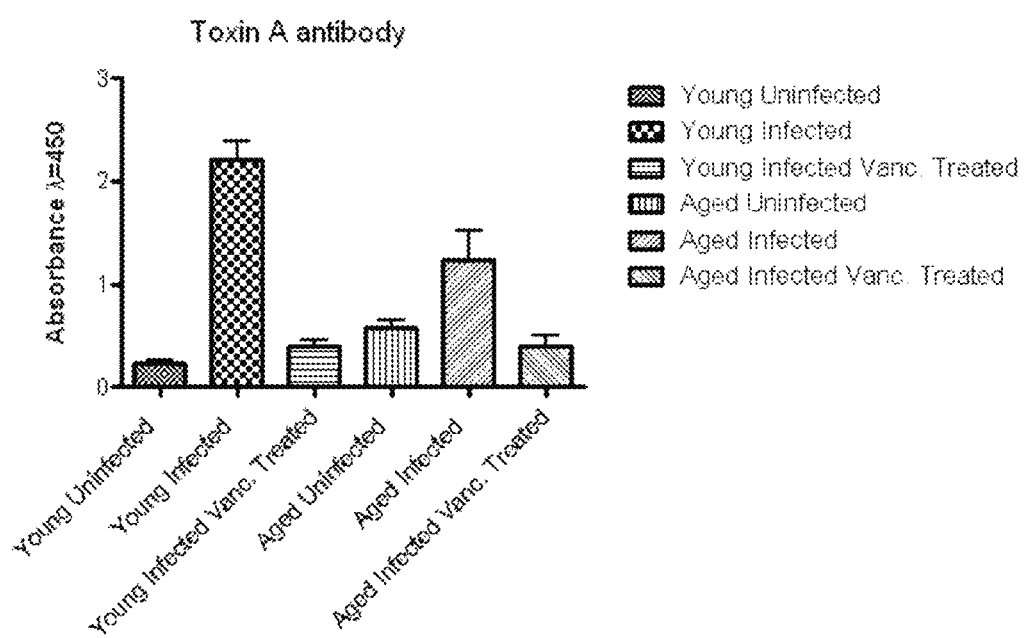
FIG. 10—Bar Graph illustrating a Toxin A antibody experiment. Ordinance—absorbance; Abscissa—young uninfected; young infected; young infected vancomycin treatment; aged uninfected; aged infected; aged infected, vancomycin treatment.

Example 2 provides additional support for the results of Example 1. The experiments in this example demonstrate that antimicrobial agents can be given as low as 1 mg/kg/day or as short as 1 day to sufficiently control diarrhea and weight loss in mice infected with *C. difficile*. Moreover, with this strategy, the intestinal gut flora is preserved and recurrent disease is prevented. Immunologic studies reveal that with standard doses of antibiotics, IgG production is reduced. Mice treated with low dose (1-20 mg) anti-*C. Difficile* agents, including vancomycin had higher IgG levels than those treated with high dose. See FIG. 10. Similar results were found with additional antibiotics (data not shown).

Example 3

Fidaxomicin at Low Doses and Short Duration

Example 3 provides additional support for the results of Examples 1 and 2.

Murine Infection Model of *Clostridium difficile* Infection

Mice were infected with *Clostridium difficile* using a model of infection similar to the one used in Warren et al. Three week old male C57BL/6 mice ordered from Jackson laboratories (Farmington, Conn.) were treated with a pre-antibiotic cocktail of vancomycin (0.0045 mg/g bodyweight), colistin (0.0042 mg/g), gentamicin (0.0035 mg/g), and metronidazole (0.0215 mg/g) for 3 days starting 6 days prior to infection. Mice were administered clindamycin (0.032 mg/g) intraperitoneally 1 day prior to infection. Antibiotics were administered pre-infection in order to make the mice susceptible to the infection. Mice were inoculated with live, vegetative *Clostridium difficile* strain VPI 10463 bacteria (ATCC) at 104 CFU. Mice were monitored for up to 14 days post-infection and checked daily for weight and clinical scoring.

Clinical scoring was based on a 0-20 point scale as described in Example 1 and takes into account the animal's weight loss, activity, posture, coat appearance, diarrhea, and eye squint/discharge.

Fidaxomicin Treatment—

Mice were administered either drug vehicle or Fidaxomicin for 5 days following infection, starting 24 hours post *C. difficile* inoculation. Fidaxomicin was purchased through the University of Virginia pharmacy. Each tablet containing 200 mg of Fidaxomicin was weighed, crushed with a mortar and pestle, and the resulting powder was weighed and added to pure Dimethyl sulfoxide (DMSO). This stock solution was diluted with varying amounts of 1% methylcellulose and DMSO to create a suspension of Fidaxomicin with a 10% DMSO/1% methylcellulose per group, the resulting was bath sonicated and vortexed vigorously in order to ensure a homogeneous mixture. Drug treatment groups were as follows: drug vehicle, 0.2 mg/kg Fidaxomicin, 2 mg/kg Fidaxomicin, 20 mg/kg Fidaxomicin all for 5 days, and a 20 mg/kg Fidaxomicin for 1 day followed by 4 days of drug vehicle. Drugs were administered 1× daily by oral gavage in a volume of 10 microliters per gram bodyweight.

Results

Example 3

FIGS. 11A-C provide three measurements of the various doses of fidaxomicin used to treat *C. difficile* infection. FIG. 11A shows the effectiveness of low doses on survival. It can be seen when comparing survival curves that low doses significantly increased survival of 2 mg/kg group compared with either the vehicle control (p=0.0191) or the 20 mg/kg/day group (p=0.0190), but not with the vehicle control compared to the 20 mg/kg/day group. In summary a lower dosage of Fidaxomicin significantly increased survival from infection compared with the drug vehicle and reduced relapse compared with a higher dosage (20 mg/kg). FIG. 11B shows the effectiveness of low doses on weight, that is, a two-way ANOVA did not find significant differences in weight across the course of the experiment; however you can see where infection starts to take hold or relapse occurs with weight drops in each group. FIG. 11C shows the effectiveness of low doses on clinical scores, that is, a two-way ANOVA performed between groups with Bonferroni correction post-test confirmed significantly less clinical scoring of mice receiving 2 mg/kg compared to mice receiving drug vehicle alone on days 3 and 5 post-infection (p<0.01), and significantly less clinical scoring of mice receiving 2 mg/kg/day compared with 20 mg/kg/day (5 days) on day 11 post-infection (p<0.001).

These results corroborate the effectiveness of low doses of vancomycin and SQ641 described above in Example 2.

CONCLUSIONS

Shorter course and lower doses of antimicrobial agents enable better immunologic responses and protection from relapse or reinfection, and likely also cause lesser alterations of the gut flora, reducing recurrent disease and ultimately, death from the infection. This strategy also cause less adverse events (toxicity from drugs) and is more economical.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

Example 1

1. Cohen S H, Gerding D N, Johnson S, Kelly C P, Loo V G, McDonald L C, Pepin J, Wilcox M H. 2010. Clinical practice guidelines for *Clostridium difficile* infection in adults: 2010 update by the Society for Healthcare Epidemiology of America (SHEA) and the Infectious Diseases Society of America (IDSA). Infect. Control Hosp. Epidemiol. 31:431-455. doi:10.1086/651706.
2. Surawicz C M, Alexander J. 2011. Treatment of refractory and recurrent *Clostridium difficile* infection. Nat. Rev. Gastroenterol. Hepatol. 8:330-339. doi:10.1038/nrgastro.2011.59.
3. Pepin J, Alary M E, Valiquette L, Raiche E, Ruel J, Fulop K, Godin D, Bourassa C. 2005. Increasing risk of relapse after treatment of *Clostridium difficile* colitis in Quebec, Canada. Clin. Infect. Dis. 40:1591-1597. doi:10.1086/430315.
4. Johnson S, Homann S R, Bettin K M, Quick J N, Clabots C R, Peterson L R, Gerding D N. 1992. Treatment of asymptomatic *Clostridium difficile* carriers (fecal excretors) with vancomycin or metronidazole. A randomized, placebo-controlled trial. Ann. Intern. Med. 117:297-302.
5. Lagrotteria D, Holmes S, Smieja M, Smaill F, Lee C. 2006. Prospective, randomized inpatient study of oral metronidazole versus oral metronidazole and rifampin for treatment of primary episode of *Clostridium difficile*-associated diarrhea. Clin. Infect. Dis. 43:547-552. doi:10.1086/506354.
6. Musher D M, Aslam S, Logan N, Nallacheru S, Bhaila I, Borchert F, Hamill R J. 2005. Relatively poor outcome after treatment of *Clostridium difficile* colitis with metronidazole. Clin. Infect. Dis. 40:1586-1590. doi:10.1086/430311.
7. Zar F A, Bakkanagari S R, Moorthi K M, Davis M B. 2007. A comparison of vancomycin and metronidazole for the treatment of *Clostridium difficile*-associated diarrhea, stratified by disease severity. Clin. Infect. Dis. 45:302-307. Abstract/FREE Full Text
8. Louie T J, Miller M A, Mullane K M, Weiss K, Lentnek A, Golan Y, Gorbach S, Sears P, Shue Y K. 2011. Fidaxomicin versus vancomycin for *Clostridium difficile* infection. N. Engl. J. Med. 364:422-431. doi:10.1056/NEJMoa0910812.
9. Garey K W, Jiang Z D, Bellard A, Dupont H L. 2008. Rifaximin in treatment of recurrent *Clostridium difficile*-associated diarrhea: an uncontrolled pilot study. J. Clin. Gastroenterol. doi:10.1097/MCG.0b013e31814a4e97.
10. Musher D M, Logan N, Mehendiratta V, Melgarejo N A, Garud S, Hamill R J. 2007. *Clostridium difficile* colitis that fails conventional metronidazole therapy: response to nitazoxanide. J. Antimicrob. Chemother. 59:705-710. doi:10.1093/jac/dk1553.
11. Chen X, Katchar K, Goldsmith J D, Nanthakumar N, Cheknis A, Gerding D N, Kelly C P. 2008. A mouse model of *Clostridium difficile*-associated disease. Gastroenterology 135:1984-1992. doi:10.1053/j.gastro.2008.09.002.
12. Warren C A, OEvan Ballard T E, Kennedy A, Wang X, Riggins M, Olekhnovich I, Warthan M, Kolling G L, Guerrant R L, Macdonald T L, Hoffman P S. 2012. Amixicile, a novel inhibitor of pyruvate:ferredoxin oxidoreductase, shows efficacy against *Clostridium difficile* in a mouse infection model. Antimicrob. Agents Chemother. 56:4103-4111. doi:10.1128/AAC.00360-12.
13. Pawlowski S W, Calabrese G, Kolling G L, Freire R, Alcantara Warren C, Liu B, Sartor B, Guerrant R L. 2010. Murine model of *Clostridium difficile* infection using gnotobiotic aged C57Bl/6 mice and a B I strain. J. Infect. Dis. 202:1708-1712.
14. Guo X, Xia X, Tang R, Zhou J, Zhao H, Wang K. 2008. Development of a real-time PCR method for Firmicutes and Bacteroidetes in faeces and its application to quantify intestinal population of obese and lean pigs. Lett. Appl. Microbiol. 47:367-373. doi:10.1111/j.1472-765X.2008.02408.x. CrossRefMedline
15. Salyers A A. 1984. *Bacteroides* of the human lower intestinal tract. Annu. Rev. Microbiol. 38:293-313. doi:10.1146/annurev.mi.38.100184.001453.
16. Herpers B L, Vlaminckx B, Burkhardt O, Blom H, Biemond-Moeniralam H S, Hornef M, Welte T, Kuijper E J. 2009. Intravenous tigecycline as adjunctive or alternative therapy for severe refractory *Clostridium difficile* infection. Clin. Infect. Dis. 48:1732-1735. doi:10.1086/599224.
17. Johnson S, Schriever C, Galang M, Kelly C P, Gerding D N. 2007. Interruption of recurrent *Clostridium difficile*-associated diarrhea episodes by serial therapy with vancomycin and rifaximin. Clin. Infect. Dis. 44:846-848. doi:10.1086/511870.
18. Musher D M, Logan N, Bressler A M, Johnson D P, Rossignol J F. 2009. Nitazoxanide versus vancomycin in *Clostridium difficile* infection: a randomized, double-blind study. Clin. Infect. Dis. 48:e41-e46. doi:10.1086/596552.
19. McFarland L V, Surawicz C M, Rubin M, Fekety R, Elmer G W, Greenberg R N. 1999. Recurrent *Clostridium difficile* disease: epidemiology and clinical characteristics. Infect. Control Hosp. Epidemiol. 20:43-50. doi:10.1086/501553. CrossRefMedline 20. Sun X, Wang H, Zhang Y, Chen K, Davis B, Feng H. 2011. Mouse relapse model of *Clostridium difficile* infection. Infect. Immun. 79:2856-2864. doi:10.1128/IAI.01336-10.
21. Hecht D W, Galang M A, Sambol S P, Osmolski J R, Johnson S, Gerding D N. 2007. In vitro activities of 15 antimicrobial agents against 110 toxigenic *Clostridium difficile* clinical isolates collected from 1983 to 2004. Antimicrob. Agents Chemother. 51:2716-2719. doi:10.1128/AAC.01623-06.
22. Baines S D, O'Connor R, Saxton K, Freeman J, Wilcox M H. 2009. Activity of vancomycin against epidemic *Clostridium difficile* strains in a human gut model. J. Antimicrob. Chemother. 63:520-525. doi:10.1093/jac/dkn502.
23. Babakhani F, Bouillaut L, Gomez A, Sears P, Nguyen L, Sonenshein A L. 2012. Fidaxomicin inhibits spore production in *Clostridium difficile*. Clin. Infect. Dis. 55(Suppl 2):S162-S169. doi:10.1093/cid/cis453.
24. Kyne L, Warny M, Qamar A, Kelly C P. 2000. Asymptomatic carriage of *Clostridium difficile* and serum levels of IgG antibody against toxin A. N. Engl. J. Med. 342:390-397.
25. Kyne L, Warny M, Qamar A, Kelly C P. 2001. Association between antibody response to toxin A and protection against recurrent *Clostridium difficile* diarrhoea. Lancet 357:189-193. doi:10.1016/S0140-6736(00)03592-3.
26. Lowy I, Molrine D C, Leav B A, Blair B M, Baxter R, Gerding D N, Nichol G, Thomas W D Jr, Leney M, Sloan S, Hay C A, Ambrosino D M. 2010. Treatment with monoclonal antibodies against *Clostridium difficile* toxins. N. Engl. J. Med. 362:197-205. doi:10.1056/NEJMoa0907635.
27. Weiss K. 2009. Toxin-binding treatment for *Clostridium difficile*: a review including reports of studies with tolevamer. Int. J. Antimicrob. Agents 33:4-7.
28. Edlund C, Barkholt L, Olsson-Liljequist B, Nord C E. 1997. Effect of vancomycin on intestinal flora of patients who previously received antimicrobial therapy. Clin. Infect. Dis. 25:729-732.
29. Louie T J, Emery J, Krulicki W, Byrne B, Mah M. 2009. OPT-80 eliminates *Clostridium difficile* and is sparing of *Bacteroides* species during treatment of *C. difficile* infection. Antimicrob. Agents Chemother. 53:261-263. doi:10.1128/AAC.01443-07.
30. Tannock G W, Munro K, Taylor C, Lawley B, Young W, Byrne B, Emery J, Louie T. 2010. A new macrocyclic antibiotic, fidaxomicin (OPT-80), causes less alteration to the bowel microbiota of *Clostridium difficile*-infected patients than does vancomycin. Microbiology 156:3354-3359. doi:10.1099/mic.0.042010-0.

BIBLIOGRAPHY

Example 2

1: Li Y, Figler R A, Kolling G, Bracken T C, Rieger J, Stevenson R W, Linden J, Guerrant R L, Warren C A. Adenosine A2A receptor activation reduces recurrence and mortality from *Clostridium difficile* infection in mice following vancomycin treatment. BMC Infect Dis. 2012 Dec. 10; 12:342. doi: 10.1186/1471-2334-12-342.

What is claimed is:

1. A method of treating a *C. difficile* infection in a subject using a short-term course of antibiotic treatment, said method comprising administering to said subject a pharmaceutical composition comprising an antibiotic effective against *C. difficile*, wherein said antibiotic is selected from the group consisting of vancomycin, fidaxomicin, metronidazole, and nitazoxanide, wherein said antibiotic is administered at a dosage ranging from about 0.1 mg/kg/day to about 20 mg/kg/day and said course of antibiotic treatment is selected from the group consisting of 1, 2, 3 and 4 days, thereby treating the *C. difficile* infection in said subject using said short term course of antibiotic treatment.

2. The method of claim 1, wherein said short-term course of antibiotic treatment is 3 or 4 days.

3. The method of claim 1, wherein said short-term course of antibiotic treatment is 1 or 2 days.

4. The method of claim 1, wherein said antibiotic is administered at a dosage ranging from 0.5 mg/kg/day to 20 mg/kg/day.

5. The method of claim 1, wherein said antibiotic is administered at a dosage selected from the group consisting of 0.1, 0.5, 1.0, 2.0, 3.0, 4.0, 5.0, 6.0, 7.0, 8.0, 9.0, 10, and 15 mg/kg/day.

6. The method of claim 1, wherein said method controls diarrhea and weight loss.

7. The method of claim 1, wherein said method reduces recurrent infection.

* * * * *